US006260966B1

(12) United States Patent
Sawano et al.

(10) Patent No.: US 6,260,966 B1
(45) Date of Patent: *Jul. 17, 2001

(54) MULTIFOCAL OCULAR LENS

(75) Inventors: Tadashi Sawano, Aichi-ken; Hiroyuki Ohyama, Kakamigahara; Kazuya Miyamura, Aichi-ken; Yuuzi Gotou, Kakamigahara; Hideaki Kondou, Okazaki, all of (JP)

(73) Assignee: Menicon Co. Ltd., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/474,740

(22) Filed: Dec. 29, 1999

Related U.S. Application Data

(63) Continuation-in-part of application No. 09/265,171, filed on Mar. 9, 1999, now Pat. No. 6,030,077.

(30) Foreign Application Priority Data

Mar. 11, 1998 (JP) .................................................... 10-59887
Jan. 7, 1999 (JP) .................................................... 11-1776

(51) Int. Cl.[7] .................................................... G02C 7/04
(52) U.S. Cl. .................................................... 351/161; 351/177
(58) Field of Search .................................. 351/160 R, 160 H, 351/161, 162, 177

(56) References Cited

U.S. PATENT DOCUMENTS

| 4,514,061 | 4/1985 | Winthrop | 351/169 |
| 4,580,882 | 4/1986 | Nuchman et aql. | 351/169 |
| 4,786,160 | 11/1988 | Fürter | 351/169 |
| 5,270,745 | 12/1993 | Pedrono | 351/169 |

FOREIGN PATENT DOCUMENTS

| 63-95415 | 4/1988 | (JP) . |
| 1-319729 | 12/1989 | (JP) . |
| 2-217818 | 8/1990 | (JP) . |
| 5-181096 | 7/1993 | (JP) . |

Primary Examiner—Scott J. Sugarman
(74) Attorney, Agent, or Firm—Burr & Brown

(57) ABSTRACT

A multifocal ocular lens having a vision correction area which includes a central and outer vision correction region, an intermediate region located between the central and outer regions, and an intermediate-distance vision correction region located radially outwardly of and adjacent to the outer region, and which has an optical axis with which centers of these regions are aligned, the central and outer vision correction regions having respective different first and second optical power values, wherein the optical power of the intermediate region located between the central and outer regions is represented by a combination of two different quadratic curves connected to each other at a point of inflection which corresponds to a desired third optical power between the first and second values, and wherein the intermediate-distance vision correction region located radially outwardly of the outer region includes radially inner and outer varying-power zones, the optical power in the radially inner varying-power zone continuously varying from the second value of the outer vision correction region to a predetermined fourth value which is between the first and second values, while the optical power in the radially outer varying-power zone continuously varying from the fourth value to the second value of the outer region.

17 Claims, 18 Drawing Sheets

MULTIFOCAL OCULAR LENS

This is a CIP application of Ser. No. 09/265,171 filed Mar. 9, 1999 now U.S. Pat. No. 6,030,077.

BACKGROUND OF THE INVENTION

1. Field of the Invention

The present invention relates in general to an ocular lens such as a contact lens placed on an eyeball or an intraocular lens inserted within the eye. More particularly, the invention is concerned with a multifocal ocular lens having a plurality of vision correction regions with different optical or vision correction powers.

2. Discussion of the Related Art

As an ocular lens used for vision correction of an eye having weakened accommodation faculty such as presbyopia, there has been proposed a bifocal or multifocal ocular lens having a plurality of vision correction regions which provide respective different optical powers. JP-A-63-95415 and JP-A-1-319729 disclose an alternating or translating vision type contact lens as one example of the multifocal ocular lens, wherein the vision correction regions with different optical powers are selectively and alternatively used as needed with a shift of the visual axis of the lens wearer. U.S. Pat. No. 4,580,882 and JP-A-2-217818 disclose a simultaneous vision type contact lens as another example of the bifocal or multifocal ocular lens, wherein the vision correction regions with different optical powers are simultaneously used, and a desired image observed through one of the vision correction regions is selected by an action of the wearer's brain.

In either of the alternating and simultaneous vision types described above, the vision correction regions of the bifocal lens consist of a near vision correction region through which near objects are observed, and a distant vision correction region through which distant objects are observed. On the other hand, the vision correction regions of the multifocal lens consist of such near and distant vision correction regions, and at least one intermediate region which is interposed between those near and distant vision correction regions and which provides an optical power different from the optical powers of the near and distant vision correction regions.

The bifocal ocular lens having the two vision correction regions, i.e., the near and distant vision correction regions, tends to suffer from a jump or overlapping of the image of an object located intermediate between near and far objects. This is because the bifocal ocular lens has only two focal points which respectively correspond to the near and distant vision correction regions. In this case, the obtained image is undesirably blurred. Further, the bifocal lens has surface discontinuity at a junction of the near and distant vision correction regions, in other words, the two vision correction regions are not smoothly connected to each other at the junction therebetween, deteriorating a wearing comfort as felt by the user.

As compared with the bifocal lens described above, the multifocal ocular lens having the intermediate region(s) between the near and distant vision correction regions provides a clearer image for the object located intermediate between the near and far objects. In the multifocal ocular lens, however, each of the plurality of vision correction regions inevitably has a small radial dimension, so that the optical power of the lens changes in steps in its radial direction, corresponding to the plurality of vision correction regions. In this case, the near and distant vision correction regions do not have sufficiently large surface areas, whereby the images to be obtained through these near and distant vision correction regions undesirably tend to be blurred. Moreover, the optical power in the multifocal lens changes in steps abruptly at each boundary between the adjacent two vision correction regions, in other words, the surfaces of the plurality of vision correction regions are not smoothly connected to one another with a continuous change of the optical power. Therefore, the multifocal lens also suffers from deteriorated wearing comfort. Further, the multifocal ocular lens tends to suffer from problems of so-called "ghosting" (ghost images) or double imaging, and mutual interference of the images obtained through the near and distant vision correction regions.

The assignee of the present invention proposed in JP-A-5-181096 a multifocal ocular lens having a near vision correction region, an intermediate region, and a distant vision correction region, which are located concentrically or coaxially with one another. In the proposed lens, the optical power continuously changes along a suitable curve from the value of one of the near and distant vision correction regions to the value of the other region. According to this arrangement, the optical power changes smoothly even at the junction of the near vision correction region and the intermediate region, and at the junction of the intermediate region and the distant vision correction region, and the lens has a smooth surface configuration which assures the user of a comfortable wearing, without having any surface discontinuity at the junctions. Further, the proposed multifocal ocular lens is free from the problem of ghosting experienced in the conventional multifocal lens wherein the vision correction regions are not smoothly connected to one another.

As a result of an extensive study by the inventors of the present invention, it was found that even the proposed multifocal ocular lens does not sufficiently meet the users' requirements. Described in detail, the proposed lens is still unsatisfactory in providing sufficiently clear viewing of both of the near and distant objects when the lens is used in specific conditions or environments by a painter and a surveying engineer, for instance.

SUMMARY OF THE INVENTION

It is a first object of the present invention to provide a multifocal ocular lens which is capable of providing sufficiently clear viewing of both near and distant visions of the user while assuring a comfortable wearing by the user.

It is a second object of the present invention to provide a multifocal ocular lens which has a high degree of freedom of design of the optical power distribution and the radial dimensions of the vision correction regions.

The above objects may be attained according to a first aspect of the present invention, which provides a multifocal ocular lens having a vision correction area consisting of a plurality of vision correction regions having respective different values of an optical power, the plurality of vision correction regions including a central vision correction region, an outer vision correction region, and an intermediate region located between the central and outer vision correction regions, the vision correction area having an optical axis with which centers of the central and outer vision correction regions are aligned, the intermediate region consisting of a radially inner transition section adjacent to the central vision correction region and a radially outer transition section adjacent to the outer vision correction region, the central and outer vision correction regions having respectively determined first and second mutually different values (Pa, Pc) of the optical power, the optical power of the intermediate region changing from the first value to the second value, such that a rate of change of the optical power of the radially inner transition section increases with an increase in a radial distance from the optical axis of the vision correction area of the lens, along a first quadratic curve, while a rate of change of the optical power of the radially outer transition section increases with an increase in a radial distance from a radially inner periphery of the outer vision correction region, along a second quadratic curve, the first and second quadratic curves being connected to each other at a point of inflection which corresponds to a radial position of a boundary between the radially inner and outer transition sections, and which corresponds to a desired third value (Pb) of the optical power between the first and second values.

In the multifocal ocular lens constructed according to the above first aspect of the invention, the central and outer vision correction regions have the respective constant values of the optical power, which are determined such that objects at desired different first and second distances can be clearly viewed. In the present multifocal ocular lens, the optical power of the intermediate region changes between the two constant values of the central and outer vision correction regions, such that the rate of change of the optical power of the intermediate region is relatively low at its radially inner and outer peripheral portions, which are adjacent to the central and outer vision correction regions, respectively, and such that the rate of change of the optical power gradually increases with an increase in the radial distances from the central and outer vision correction regions. This arrangement assures a high degree of clearness of images obtained through the central and outer vision correction regions, without being adversely influenced by the presence of the intermediate region.

In the present multifocal ocular lens wherein the intermediate region consists of the radially inner transition section adjacent to the central vision correction region and the radially outer transition section adjacent to the outer vision correction region, the optical power of the intermediate region changes such that the rates of change of the optical power of the radially inner and outer transition sections are respectively represented by the first and second quadratic curves which are connected to each other at the point of inflection that corresponds to the radial position of the boundary between the radially inner and outer transition sections. Unlike an intermediate region providing an optical power which changes along a single curve represented by an inverse function of third degree or order, the intermediate region of the present multifocal ocular lens designed as described above provides the optical power which smoothly and continuously changes between the optical power values of the central and outer vision correction regions, irrespective of the optical power values and the sizes or surface areas of the central and outer vision correction regions. This arrangement assures a high degree of freedom in determining the lens power distribution and the surface areas or radial dimensions of the central and outer vision correction regions, without suffering from any bend or discontinuity on the lens surface.

In a first preferred form of the above first aspect of the invention, a value y1 of the optical power of the radially inner transition section at a radial point which is distant from the optical axis of said vision correction area of the lens by a radial distance x1 is represented by the following equation (1), while a value y2 of the optical power of the radially outer transition section at a radial point which is distant from the optical axis of the vision correction area by a radial distance x2 is represented by the following equation (2), $$y1 = Pa - (Pa - Pb) \times (Wa - x1)^2 / (Wa - Wb)^2 \quad (1)$$

$$y2 = Pc - (Pc - Pb) \times (Wc - x2)^2 / (Wc - Wb)^2 \quad (2)$$

wherein,

Pa: the first value of the optical power of the central vision correction region, Pc: the second value of the optical power of the outer vision correction region, Pb: the third value of the optical power at the radial position of the boundary between the radially inner and outer transition sections, Wa: a radial distance from the optical axis of the vision correction area to a boundary between the central vision correction region and the radially inner transition section, Wb: a radial distance from the optical axis of the vision correction area to the boundary between the radially inner and outer transition sections, and Wc: a radial distance from the optical axis of the vision correction area to a boundary of the radially outer transition section and the outer vision correction region.

This arrangement provides the multifocal ocular lens whose intermediate region is smoothly continuously connected to the central and outer vision correction regions. In particular, the lens surface is designed such that the optical power of the intermediate region smoothly continuously changes to the constant values of the central and outer vision correction regions, at a junction of the central vision correction region and the radially inner transition section, and at a junction of the outer vision correction region and the radially outer transition section. The thus designed ocular lens assures the user of a comfortable wearing while effectively avoiding the problem of double imaging or ghosting.

In one advantageous arrangement of the above first preferred form of the invention, the radial distance Wb from the optical axis of the vision correction area to the boundary of the radially inner and outer transition sections is determined according to the following equation:

$$Wb = ((Pa - Pb)Wc - (Pc - Pb)Wa) / (Pa - Pc) \quad (3)$$

In the above arrangement wherein the radial position of the boundary between the radially inner and outer transition sections is determined based on the above equation, the lens surface is designed such that the optical power smoothly continuously changes at the peripheral portions of the intermediate region near the above-indicated boundary, resulting in improved wearing comfort of the lens as felt by the user and enhanced vision correction performance of the lens.

In another advantageous arrangement of the above first preferred form of the first aspect of the invention, the central vision correction region constitutes a part of a central optical zone for correction of a near vision, while the outer vision correction region constitutes a part of a peripheral optical zone for correction of a distant vision, and values Pa, Pb, Pc, Wa, Wb and Wc in said equations (1) and (2) are determined as follows:

$$Pa = P + ADD \quad (4)$$

$$P + (\tfrac{1}{6})ADD \leq Pb \leq P + (\tfrac{2}{3})ADD \quad (5)$$

$$Pc = P \quad (6)$$

$$Wa = (\tfrac{1}{2})SD \quad (7)$$

$$(\tfrac{1}{2})SD + (\tfrac{1}{8})IM \leq Wb \leq (\tfrac{1}{2})SD + (\tfrac{1}{2})IM \quad (8)$$

$$Wc = (1/2)SD + IM \tag{9}$$

$$0.1 \text{ mm} \leq IM \leq 3.5 \text{ mm} \tag{10}$$

$$0 \leq SD \leq 8.0 \text{ mm} \tag{11}$$

wherein,
ADD: a difference between Pa and Pc,
IM: a radial dimension of the intermediate region,
SD: a diameter of the central optical zone (segment diameter), and
OZ: a diameter of the peripheral optical zone.

In still another advantageous arrangement of the above first preferred form of the first aspect of the invention, the central vision correction region constitutes a part of a central optical zone for correction of a distant vision, while the outer vision correction region constitutes a part of a peripheral optical zone for correction of a near vision, and values Pa, Pb, Pc, Wa, Wb and Wc in said equations (1) and (2) are determined as follows:

$$Pa = P \tag{12}$$

$$P + (1/6)ADD \leq Pb \leq P + (2/3)ADD \tag{13}$$

$$Pc = P + ADD \tag{14}$$

$$Wa = (1/2)SD \tag{15}$$

$$(1/2)SD + (1/2)IM \leq Wb \leq (1/2)SD + (7/8)IM \tag{16}$$

$$Wc = (1/2)SD + IM \tag{17}$$

$$0.1 \text{ mm} \leq IM \leq 3.5 \text{ mm} \tag{18}$$

$$0 \leq SD \leq 8.0 \text{ mm} \tag{19}$$

wherein,
ADD: a difference between Pa and Pc,
IM: a radial dimension of the intermediate region,
SD: a diameter of the central optical zone (segment diameter), and
OZ: a diameter of the peripheral optical zone.

By designing the multifocal ocular lens based on the above formulas (4) through (11), the central optical zone provides a near vision correction power suitable for viewing the near objects, while the peripheral optical zone provides a distant vision correction power suitable for viewing the distant objects. By designing the multifocal ocular lens based on the above formulas (12) through (19), the central optical zone provides a distant vision correction power suitable for viewing the distant objects, while the peripheral optical zone provides a near vision correction power suitable for viewing the near objects. In either of the multifocal ocular lenses designed based on the formulas (4)–(11) and the formulas (12)–(19), respectively, the radial position of the boundary between the radially inner and outer transition sections of the intermediate region, i.e., the point of inflection at which the first and second quadratic curves are connected to each other, is located at a position of the intermediate region on the side of the near vision correction region. This arrangement effectively assures a high degree of clearness of images of both of the near objects and the distant objects under the normal wearing conditions of the lens.

In a second preferred form of the above first aspect of the invention, the optical axis of the vision correction area of the lens is offset from a geometric center axis of the lens in a lateral direction by a distance of not larger than 2.0 mm.

When the present multifocal ocular lens is used as a contact lens, the above arrangement assures a significantly high degree of clear viewing of the objects since the optical axis of the vision correction area is aligned with the center of the pupil of the user's eye when the contact lens is worn on the eye of the user. In other words, this arrangement takes into account of a fact that the contact lens tends to be positioned at a portion of the cornea on the side of the ear, with the geometric center axis of the lens being offset from the center of the pupil on the side of the ear, since the cornea of the human eye has a larger curvature at a portion on the side of the ear than the other portion on the side of the nose.

In a third preferred form of the above first aspect of the invention, the central vision correction region constitutes a part of a central optical zone for correction of a near vision, while the outer vision correction region constitutes a part of a peripheral optical zone for correction of a distant vision, the optical axis of the vision correction area of the lens being offset from a geometric center axis of the lens in a downward direction by a distance of not larger than 7.0 mm.

In a fourth preferred form of the above first aspect of the invention, the central vision correction region constitutes a part of a central optical zone for correction of a distant vision, while the outer vision correction region constitutes a part of a peripheral optical zone for correction of a near vision, the optical axis of the vision correction area of the lens being offset from a geometric center axis of the lens in an upward direction by a distance of not larger than 7.0 mm.

By shifting or offsetting the optical center axis of the vision correction area from the geometric center axis of the lens in suitable directions as described above, the optical zone for near vision correction and the optical zone for distant vision correction, which have the common optical axis, can be selectively and alternatively used, depending upon the position of the pupil of the eye. Described in detail, the position of the pupil when the visual axis of the lens wearer is directed frontwards for viewing the distant objects is different from the position of the pupil when the visual axis of the lens wearer is directed downwards for viewing the near objects. Accordingly, depending upon the position of the pupil of the eye, the optical zone for near vision correction and the optical zone for distant vision correction are selectively used, so that the multifocal ocular lens of this arrangement is used as a translating vision type ocular lens.

In a fifth preferred form of the above first aspect of the invention, at least one of opposite surfaces of the lens has part-spherical portions corresponding to the central and outer vision correction regions. This arrangement permits easy design of the lens surface, so that the multifocal ocular lens having excellent optical properties can be easily fabricated. In a contact lens, for instance, one of its opposite surfaces, generally the inner concave surface is formed to have a part-spherical profile following that of a front surface of the cornea of the user's eye, while the other convex surface is formed to give a desired vision correction power.

In a sixth preferred form of the above first aspect of the present invention, either one of opposite surfaces of the lens has a toric portion corresponding to the vision correction area. In a contact lens wherein one of its opposite surfaces is formed to be a part-spherical concave surface having a profile following that of a front surface of the eyeball, the toric portion may be formed on the other surface which is a part-spherical convex surface that gives a desired vision correction power with the vision correction regions (central, intermediate, and outer regions) being suitably formed. In this case, the optical power values of the central and outer vision correction regions vary in the circumferential direction of the lens depending on the cylinder axis orientation of the toric portion, while the optical power values of the central and outer vision correction regions are constant in diametric directions of the lens.

The above-indicated objects of the present invention indicated above may also be attained according to a second aspect of the invention, which provides a multifocal ocular lens having a vision correction area consisting of a plurality of vision correction regions having respective different values of optical power, the plurality of vision correction regions including a central vision correction region, an outer vision correction region, and an intermediate region located between the central and outer vision correction regions, the vision correction area having an optical axis with which centers of the central and outer vision correction regions are aligned, the intermediate region consisting of a radially inner transition section adjacent to the central vision correction region and a radially outer transition section adjacent to the outer vision correction region, the central and outer vision correction regions having respectively determined first and second mutually different optical power values (Pa, Pc), the optical power of the intermediate region changing from the first value to the second value, such that a rate of change of the optical power of the radially inner transition section increases with an increase in a radial distance from the optical axis of the vision correction area of the lens, along a first quadratic curve, while a rate of change of the optical power of the radially outer transition section increases with an increase in a radial distance from a radially inner periphery of the outer vision correction region, along a second quadratic curve, the first and second quadratic curves being connected to each other at a point of inflection which corresponds to a radial position of a boundary between the radially inner and outer transition sections, and which corresponds to a desired third optical power value (Pb) between the first and second values, and wherein the optical axis of the vision correction area of the lens is offset from a geometric center axis of the lens in a lateral direction by a distance of not larger than 2.0 mm, and also in a vertical direction by a distance of not larger than 7.0 mm.

The above-indicated objects of the present invention indicated above may also be attained according to a third aspect of the invention, which provides a multifocal ocular lens having a vision correction area consisting of a plurality of vision correction regions having respective different values of optical power, the plurality of vision correction regions including a central vision correction region, an outer vision correction region, and an intermediate region located between the central and outer vision correction regions, the vision correction area having an optical axis with which centers of the central and outer vision correction regions are aligned, the intermediate region consisting of a radially inner transition section adjacent to the central vision correction region and a radially outer transition section adjacent to the outer vision correction region, the central and outer vision correction regions having respectively determined first and second mutually different optical power values (Pa, Pc), the optical power of the intermediate region changing from the first value to the second value, such that a rate of change of the optical power of the radially inner transition section increases with an increase in a radial distance from the optical axis of the vision correction area of the lens, along a first quadratic curve, while a rate of change of the optical power of the radially outer transition section increases with an increase in a radial distance from a radially inner periphery of the outer vision correction region, along a second quadratic curve, the first and second quadratic curves being connected to each other at a point of inflection which corresponds to a radial position of a boundary between the radially inner and outer transition sections, and which corresponds to a desired third optical power value (Pb) between the first and second values, the vision correction area further including an intermediate-distance vision correction region located radially outwardly of and adjacent to the outer vision correction region and having a distribution of optical power between the first and second values (Pa, Pc) of the central and outer vision correction regions, respectively, and wherein the intermediate-distance vision correction region comprises a radially inner varying-power zone and a radially outer varying-power zone, and the optical power in the radially inner varying-power zone continuously varying in a radial direction of the lens from the second optical power value (Pc) of the outer vision correction region to a predetermined fourth optical power value (Pd) which is between the first and second optical power values (Pa, Pc) of the central and outer vision correction regions, while the optical power in the radially outer varying-power zone continuously varies in the radial direction from the fourth optical power value (Pd) to the second optical power value (Pc) of the outer vision correction region.

In the multifocal ocular lens constructed according to the above third aspect of the invention, the vision correction area further includes the intermediate-distance vision correction region which is located radially outwardly of and adjacent to the outer vision correction region. This intermediate-distance vision correction region has a distribution of optical power between the first and second optical power values (Pa, Pc) of the central and outer vision correction regions, respectively, and comprises the radially inner varying-power zone and the radially outer varying-power zone. The optical power in the radially inner varying-power zone continuously varies in the radial direction of the lens from the second optical power value (Pc) of the outer vision correction region to the predetermined fourth value (Pd) which is between the first and second values (Pa, Pc), while the optical power in the radially outer varying-power zone continuously varies in the radial direction of the lens from the fourth optical power value (Pd) to the second optical power value (Pc) of the outer vision correction region. Like the intermediate region located between the central and outer vision correction regions, the thus formed intermediate-distance vision correction region is effective to reduce or avoid the problem of ghosting or double imaging, so that the present multifocal ocular lens assures a high degree of visual acuity of objects at the desired two different distances, i.e., near and far distances or vice versa, to which the first and second optical power values (Pa, Pc) of the central and outer vision correction regions are tuned.

Owing to the presence of the intermediate-distance vision correction region having the advantages described above, the radial dimension of the intermediate region located between the central and outer vision correction regions can be reduced, whereby the outer vision correction region located radially outwardly of and adjacent to the intermediate region can be shifted in a radially inward direction closer to the optical center axis of the vision correction area. It is known that the lens exhibits higher optical performance at its central portion which is relatively close to the optical center axis than its peripheral portion which is remote from the optical center axis. Accordingly, the outer vision correction region shifted towards the optical center axis assures enhanced optical characteristics. Further, the outer vision correction region shifted towards the optical center axis is capable of covering a larger area of the pupil of the user's eye, assuring a higher degree of visual acuity of objects observed through the outer vision correction region.

In the present multifocal ocular lens, the intermediate-distance vision correction region has the desired fourth optical power value (Pd) which is intermediate between the first and second optical power values (Pa, Pc) of the central and outer vision correction regions, which central and outer regions are used as a distant and a near vision correction region or vice versa. Accordingly, the present multifocal ocular lens having the thus formed intermediate-distance vision correction region assures a high degree of visual acuity of objects at the desired particular intermediate distance to which the fourth optical power value (Pd) is tuned.

In preferred forms of the above third aspect of the present invention, a value y3 of the optical power in the radially inner varying-power zone is represented by the following equation (20), and a value y4 of the optical power in the radially outer varying-power zone is represented by the following equation (21):

$$y3 = E1 \cdot (x^3/3 - x^2(Wd+We)/2 + x \cdot Wd \cdot We) + F1 \qquad (20)$$

$$y4 = E2 \cdot (x^3/3 - x^2(Wf+Wg)/2 + x \cdot Wf \cdot Wg) + F2 \qquad (21)$$

wherein, $$E1 = (Pc-Pd)/((Wd^3-We^3)/3 - (Wd^2-We^2)(Wd+We)/2 + (Wd-We) \cdot Wd \cdot We)$$

$$F1 = Pc - E1 \cdot (Wd^3/3 - Wd^2(Wd+We)/2 + Wd \cdot Wd \cdot We)$$

$$E2 = (Pd-Pc)/((Wf^3-Wg^3)/3 - (Wf^2-Wg^2)(Wf+Wg)/2 + (Wf-Wg) \cdot Wf \cdot Wg)$$

$$F2 = Pd - E2 \cdot (Wf^3/3 - Wf^2(Wf+Wg)/2 + Wf \cdot Wf \cdot Wg)$$

and wherein, x: a radial distance from the optical axis of the vision correction area;
Wd: a radial distance from the optical axis to a boundary between the outer and intermediate-distance vision correction regions;
We: a radial distance from the optical axis to a radially outer end of the radially inner varying-power zone;
Wf: a radial distance from the optical axis to a radially inner end of the radially outer varying-power zone;
Wg: a radial distance from the optical axis to a radially outer end of the radially outer varying-power zone;
Pc: the second optical power value of the outer vision correction region;
Pd: the fourth optical power value in the intermediate-distance vision correction region.

The above-indicated objects of the present invention indicated above may also be attained according to a fourth aspect of the invention, which provides a multifocal ocular lens having a vision correction area which consists of a plurality of vision correction regions having respective different values of an optical power, the plurality of vision correction regions including a central vision correction region, an outer vision correction region, and an intermediate region located between the central and outer vision correction regions, the vision correction area having an optical axis with which centers of the central and outer vision correction regions are aligned, the central and outer vision correction regions having respectively determined first and second mutually different values (Pa, Pb) of the optical power, the optical power of the intermediate region being represented by one polynomial equation whose degree "exp" is not smaller than 2, and continuously changing from the first value to the second value with an increase in a radial distance from the optical axis of the vision correction area of the lens.

In the multifocal ocular lens constructed according to the above fourth aspect of the invention, the central and outer vision correction regions have the respective different constant values of the optical power, which are determined such that objects at desired different first and second distances can be clearly viewed. Further, the present multifocal ocular lens wherein the optical power of the intermediate region continuously or gradually changes from the first value of the central vision correction region to the second value of the outer vision correction region, is capable of assuring a high degree of clearness of images obtained through the central and outer vision correction regions.

In the present multifocal ocular lens wherein the optical power of the intermediate region is represented by one polynomial function whose degree or order is not smaller than 2 so that the optical power continuously changes from the first value of the central vision correction region to the second value of the outer vision correction region, the radially inner portion of the intermediate region is smoothly connected to the central vision correction region while the radially outer portion of the intermediate region is smoothly connected to the outer vision correction region. Unlike the conventional ocular lens having an intermediate region whose optical power linearly changes, the present ocular lens assures a high degree of freedom of design of the optical power and the radial dimension of the intermediate region, resulting in a considerably high degree of freedom in determining the optical power distribution of the ocular lens as a whole.

In the present multifocal ocular lens having the intermediate region whose optical power continuously or gradually changes from the first value of the central vision correction region to the second value of the outer vision correction region with an increase of the radial distance from the optical axis of the vision correction area, the optical power of the ocular lens does not have its maximum or minimum value in the intermediate region. Namely, the optical power of the intermediate region changes such that it gradually increases or decreases from the first value to the second value with the increase of the radial distance from the optical axis of the vision correction area.

In a first preferred form of the above fourth aspect of the present invention, the degree "exp" of the polynomial equation which represents the optical power of the intermediate region and a radial dimension "IM" (mm) of the intermediate region are determined so as to satisfy the following formulas (22) and (23), respectively, while a diameter "SD" (mm) of a central optical zone which is constituted by the central vision correction region is determined so as to satisfy the following formula (24):

$$2 \leq \exp \leq 20 \qquad (22)$$

$$\exp/20 \leq IM \leq 2.0 + \exp/5 \qquad (23)$$

$$0.2 \leq SD \leq 3.0 \qquad (24)$$

In the multifocal ocular lens constructed according to the above first preferred form of the fourth aspect of the invention, the problem of so-called "ghosting" or double imaging conventionally experienced due to the presence of the intermediate region between the center and outer vision correction regions is prevented or minimized. In addition, by adjusting the rate of change of the optical power of the intermediate region, the vision correction function achieved by the central and outer vision correction regions can be advantageously tuned or adjusted as desired. Described more specifically, if the degree "exp" of the polynomial equation which represents the optical power of the intermediate region is made relatively large (e.g., exp=7 or larger), it results in an increase in the rate of change of the optical power of the intermediate region, so that the central and outer vision correction regions may have sufficiently large radial dimensions, whereby the central and outer vision correction regions can provide one and the other of the near vision correction power and the distant vision correction power with high stability. For clear viewing of the distant and near objects respectively obtained through one and the other of the central and outer vision correction regions of the ocular lens, and for comfortable wearing of the ocular lens as felt by the users, the degree "exp" of the polynomial equation is preferably determined so as to satisfy the following formula (25):

$$4 \leq \exp \leq 8 \tag{25}$$

In a second preferred form of the above fourth aspect of the present invention, the optical axis of the vision correction area is offset from a geometric center axis of the lens in a lateral direction by a distance of not larger than 2.0 mm. This arrangement offers the advantages similar to those described above with regard to the second preferred form of the above first aspect of the invention.

In a third preferred form of the above fourth aspect of the invention, the central vision correction region constitutes a part of a central optical zone for correction of a near vision, while the outer vision correction region constitutes a part of a peripheral optical zone for correction of a distant vision, the optical axis of the vision correction area being offset from a geometric center axis of the lens in a downward direction by a distance of not larger than 7.0 mm. This arrangement offers the advantages similar to those described above with regard to the third preferred form of the above first aspect of the invention.

In a fourth preferred form of the fourth aspect of the present invention, the central vision correction region constitutes a part of a central optical zone for correction of a distant vision, while the outer vision correction region constitutes a part of a peripheral optical zone for correction of a near vision, the optical axis of the vision correction area being offset from a geometric center axis of the lens in an upward direction by a distance of not larger than 7.0 mm. This arrangement provides the advantages similar to those described above with respect to the fourth preferred form of the above first aspect of the invention.

In a fifth preferred form of the fourth aspect of the present invention, at least one of opposite surfaces of the lens has part-spherical portions corresponding to the central and outer vision correction regions. This arrangement provides the advantages similar to those described above with respect to the fifth preferred form of the above first aspect of the invention.

In a sixth preferred form of the fourth aspect of the present invention, either one of opposite surfaces of the lens has a toric portion corresponding to the vision correction area. This arrangement provides the advantages similar to those described above with respect to the sixth preferred form of the above first aspect of the invention.

BRIEF DESCRIPTION OF THE DRAWINGS

The above and optional objects, features, advantages and technical significance of the present invention will be better understood by reading the following detailed description of presently preferred embodiments of the invention, when considered in conjunction of the accompanying drawings, in which.

DETAILED DESCRIPTION OF THE PREFERRED EMBODIMENTS

Figure 1:
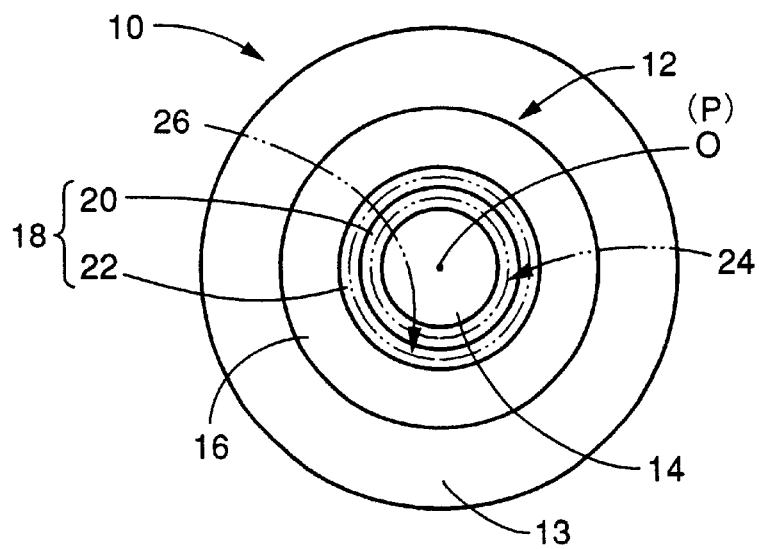
FIG. 1 is a plan view of a contact lens according to one embodiment of the present invention.

Referring first to FIG. 1, there is shown a multifocal ocular lens in the form of a contact lens 10 for correction of presbyopia, for instance, which lens is constructed according to one embodiment of the present invention. This contact lens 10 includes a vision correction area 12 whose optical axis P is aligned with a geometric center axis O of the lens, which is a center of a circle defined by the periphery of the lens. A portion 13 radially outward of the vision correction area 12, in other words, the radially outermost portion 13 of the contact lens 10 is not to be located on the pupil of the eye of the user when the contact lens 10 is worn on the eye. Accordingly, this radially outermost portion 13 does not have any optical significance, but is provided for easy and stable fitting of the lens on the eye. The portion 13 of the lens 10 is subjected to a slab-off machining as needed.

The vision correction area 12 includes a circular central vision correction region 14 whose center is aligned with the above-described optical axis P, an annular outer vision correction region 16 located concentrically with and radially outwardly of the central vision correction region 14 with a suitable radial distance therebetween, and an annular intermediate vision correction region 18 located concentrically with and interposed between the central and outer vision correction regions 14, 16. These three regions 14, 16, 18 have respectively determined mutually different values of optical power.

The central and outer vision correction regions 14, 16 have respective constant values of optical power which are different from each other. Depending upon the user's visual requirements and lifestyle or living environment, for example, the central and outer vision correction regions 14, 16 are used, respectively, as one and the other of a near vision correction region for correcting the user's near vision, through which near objects are observed, and a distant vision correction region for correcting the user's distant vision, through which distant objects are observed. The intermediate vision correction region 18 has a varying optical power, which gradually varies in the radial direction of the lens, such that the optical power smoothly changes between the mutually different optical power values of the central and outer vision correction regions 14, 16. That is, the optical power of the lens 10 continuously changes from that of the central vision correction region 14 to that of the outer vision correction region 16 via the continuously varying optical power of the intermediate region 18. Described in detail, the intermediate region 18 consists of a radially inner transition section 20 adjacent to the central vision correction region 14, and a radially outer transition section 22 adjacent to the outer vision correction region 16.

The optical powers of the central and outer vision correction regions 14, 16 are represented by respective different algebraic equations or expressions of the zeroth degree or order in relation to the radial distance from the optical axis P. In other words, the optical powers of the central and outer vision correction regions 14, 16 are constant, irrespective of a change of the radial distance from the optical axis P. The optical power of the intermediate region 18 is represented by a combination of two quadratic expressions or equations (polynomial equation of the second degree or order) in relation to the radial distance from the optical axis P. Described more precisely, these quadratic equations have respective terms of the second degree whose signs are opposite to each other. The two quadratic equations represent respective two quadratic curves, one of which is a concave curve, and the other of which is a convex curve. The optical powers of the radially inner and outer transition sections 20, 22 of the intermediate region 18 are represented by portions of one and the other of those concave and convex quadratic curves.

Figure 2:
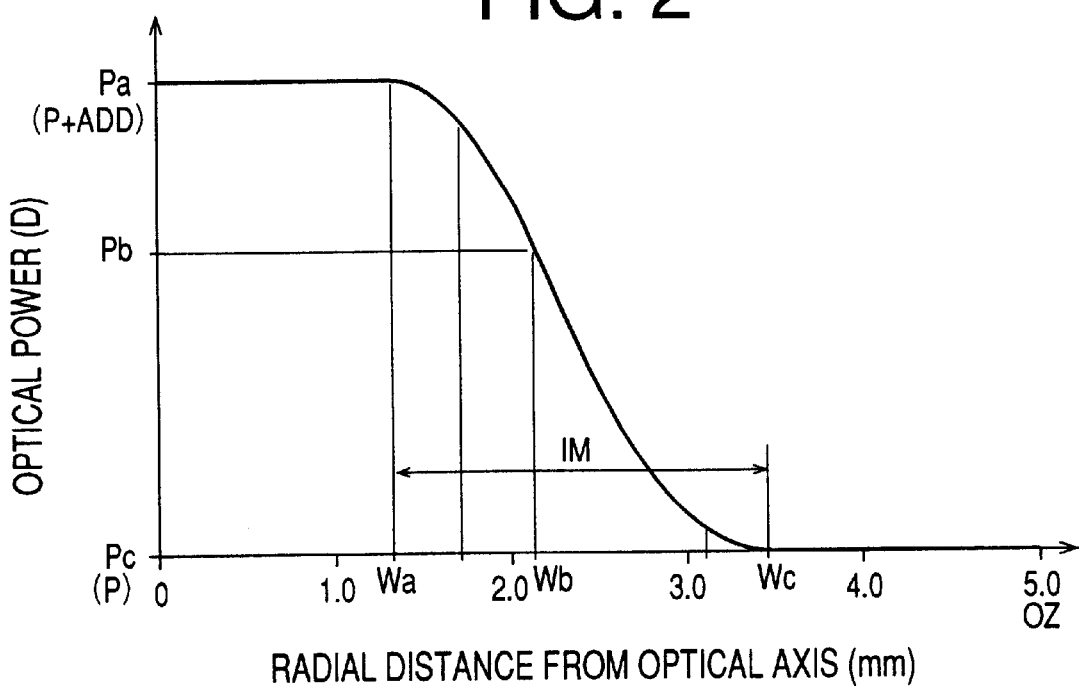
FIG. 2 is a graph showing one example of a distribution of the optical power of the contact lens of FIG. 1, in the radial direction.

Described more specifically, when the central vision correction region 14 functions as the near vision correction region and the outer vision correction region 16 functions as the distant vision correction region, the values of the optical power of the vision correction regions 12, 14, 16 are preferably determined based on the above formulas (1), (2) and (4)–(11). One example of the lens power distribution determined according to the above formulas is shown in the graph of FIG. 2. As is apparent from the graph, the central vision correction region 14 which has a constant optical power Pa constitutes a substantial part of a central optical zone 24 of the lens 10 used for near vision correction, while the outer vision correction region 16 which has a constant optical power Pc constitutes a substantial part of a peripheral optical zone 26 of the lens 10 for distant vision correction. Accordingly, the thus designed contact lens 10 is capable of assuring a high degree of clearness of images of both of the near and distant objects observed through the central and peripheral optical zones 24, 26, respectively. The radial dimensions of the vision correction regions 14, 16, 18 are suitably determined so as to meet the user's visual requirements, and assure the user of a comfortable wearing or fitting of the lens, while satisfying the above formulas (1), (2) and (4)–(11).

The configuration of the contact lens 10 whose optical power is designed as described above is determined such that the inner surface to be in contact with the cornea of the user's eye has a part-spherical profile following that of the cornea, and such that the outer surface is shaped according to a ray tracing method, so as to give an intended optical power distribution.

As is apparent from the graph of FIG. 2, the optical power of the intermediate region 18 is determined such that the optical power of the radially inner transition section 20 and the optical power of the radially outer transition section 22 are respectively represented by the two quadratic curves which are connected to each other at the point of inflection that corresponds to the radial position of the boundary between the radially inner and outer transition regions 20, 22. According to this arrangement, the optical power of the lens 10 smoothly continuously decreases from the value Pa of the central vision correction region 14 to the value Pc of the outer vision correction region 16 via the continuously varying optical power of the intermediate region 18. The thus designed contact lens 10 has a smooth surface configuration, assuring the user of its comfortable wearing. Further, the present contact lens 10 does not suffer from the problems of scattering of light and the double imaging or ghosting at the connected portions of the central vision correction regions 14, the intermediate region 18, and the outer vision correction region 16, to thereby assure clear images obtained through these vision correction regions designed as described above.

Figure 3:
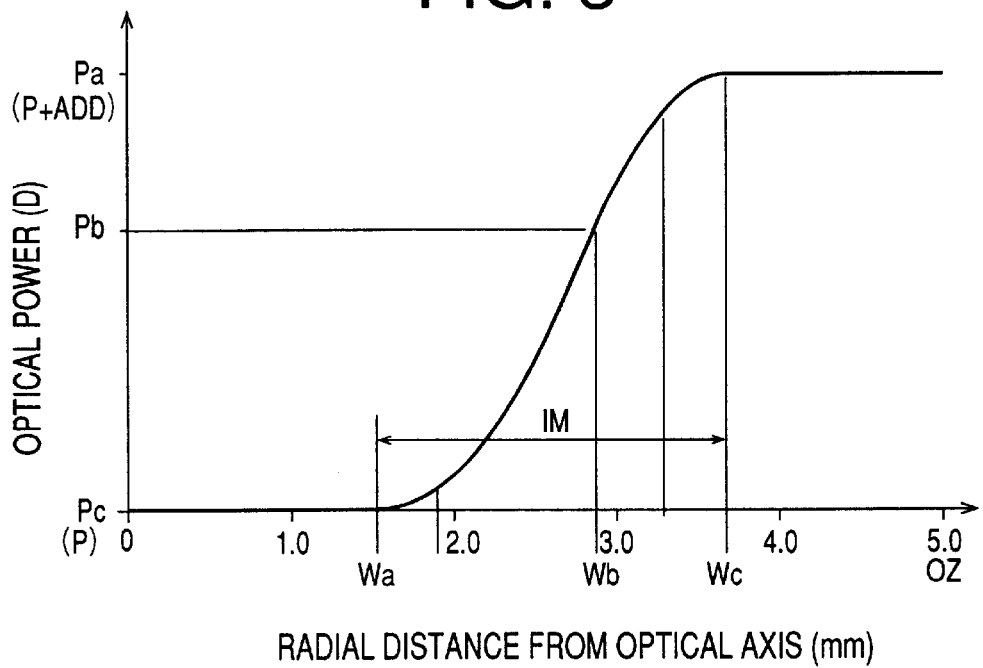
FIG. 3 is a graph showing another example of the distribution of the optical power of the contact lens of FIG. 1, in the radial direction.

When the central vision correction region 14 serves as the distant vision correction region, and the outer vision correction region 16 serves as the near vision correction region, the optical power values of the three vision correction regions are preferably determined on the basis of the above formulas (1), (2) and (12) through (19). One example of the lens power distribution determined according to the above formulas is shown in a graph of FIG. 3. As apparent from the graph, the central vision correction region 14 which has the constant optical power Pc constitutes a substantial part of the central optical zone 24 used for distant vision correction, while the outer vision correction region 16 which has the constant optical power Pa constitutes a substantial part of the peripheral optical zone 26 used for near vision correction. According to this arrangement, the optical power of the lens 10 smoothly continuously increases from the value Pc of the central vision correction region 14 to the value Pa of the outer vision correction region 16 via the continuously varying optical power of the intermediate region 18. The thus designed contact lens also assures clear viewing of both of the near and distant objects through the peripheral and central optical zones 26, 24, respectively. Further, the central vision correction region 14 and the outer vision correction region 16 are smoothly connected to each other with the intermediate region 18 interposed therebetween, to thereby assure the user of a good wearing comfort and clear viewing of the objects through these vision correction regions 14, 16, 18.

In the contact lens 10 shown in FIG. 1, the optical axis P of the vision correction area 12 is aligned with the geometrical center axis O of the contact lens 10. However, the optical axis P may be offset from the geometrical center axis O, as needed. In this case, depending upon the offset distance of the optical axis P from the geometrical center axis O, and the radial dimensions of the respective vision correction regions 14, 16, 18, the circular vision correction area 12 may be partly removed at its radially outer peripheral portion, generally, at the radially outer peripheral portion of the outer vision correction region 16, but possibly at the radially outer peripheral portion of the intermediate vision correction region 18, and even at the radially outer peripheral portion of the central vision correction region 14.

Figure 4:
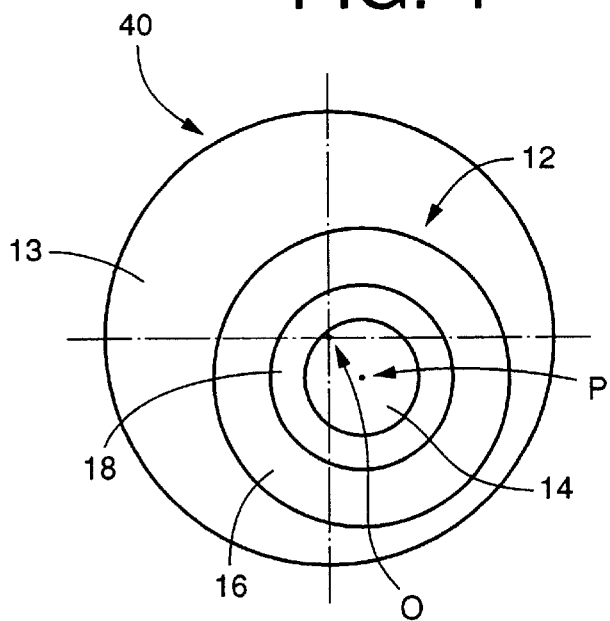
FIG. 4 is a plan view of a contact lens according to another embodiment of the invention.

For instance, the optical axis P of the vision correction area 12 of a contact lens 40 is offset from the geometrical center axis O as shown in FIG. 4, such that the optical axis P is shifted in the right direction as seen in FIG. 4, on the side of the nose of the wearer when the contact lens is worn on the eye, and is also shifted in the downward direction. The optical axis P is shifted from the geometrical center axis O of the lens on the side of the nose of the lens wearer, in view of a fact that the contact lens tends to be moved toward a portion of the cornea on the side of the ear of the wearer when the lens is worn on the eye, since the cornea of the human eye has a larger curvature at the portion on the side of the ear than the other portion on the side of the nose. Further, the optical axis P is shifted from the geometrical center axis O of the lens in the downward direction, in view of a tendency that the visual axis of the lens wearer usually is directed downwards in the ordinary daily life. When the contact lens whose optical axis P is offset from its geometric center axis O as described above is worn on the eye of the user, the optical axis P is easily aligned with the center of the pupil, so that the contact lens effectively achieves the intended vision correction function. For easy understanding, the same reference numerals as used in the contact lens 10 of FIG. 1 are used to identify the corresponding portions of the contact lens 40 of FIG. 4.

Though the contact lenses 10, 40 of the above-described embodiments are the simultaneous vision type, the multifocal ocular lens of the present invention is also used as a translating vision type ocular lens, by suitably determining the offset distance of the optical axis of the vision correction regions 14, 16, 18 (vision correction area 12) from the geometric center axis of the lens, and the size or the radial dimensions of the respective vision correction regions.

Figure 5:
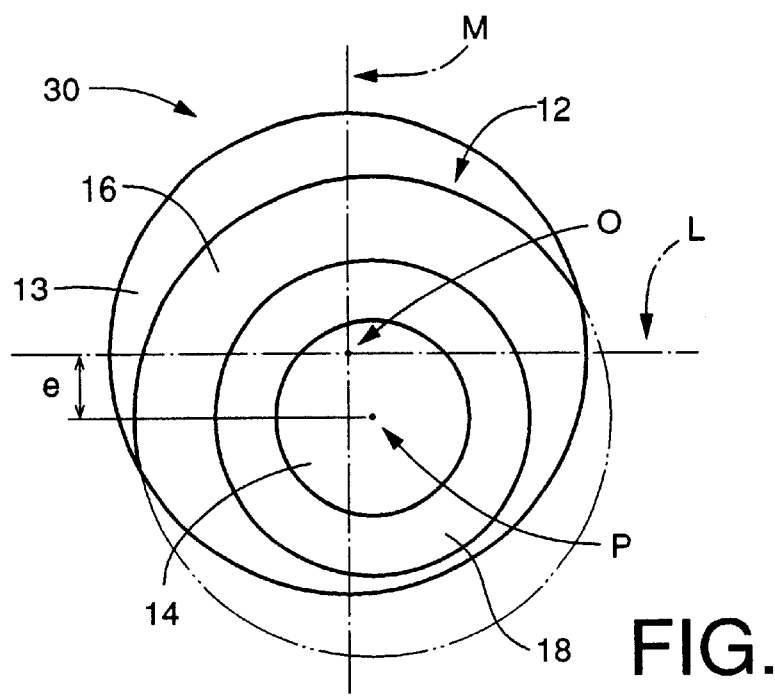
FIG. 5 is a plan view of a contact lens according to still another embodiment of the invention.

Referring to FIG. 5, there is shown another embodiment of the multifocal ocular lens according to the present invention, in the form of a translating vision type contact lens 30. In the contact lens 30 of this embodiment, the central vision correction region 14 is used as the near vision correction region while the outer vision correction region 16 is used as the distant vision correction region. The vision correction area 12 which consists of the central, intermediate and outer vision correction regions 14, 16, 18 has an optical axis P which is offset from the geometric center axis O of the lens in the downward direction as seen in FIG. 5, wherein a line indicated by "L" is a horizontal line passing the geometric center axis O of the lens, and a line indicated by "M" is a vertical line also passing the geometric center axis O.

When the visual axis of the wearer who wears the thus constructed contact lens 30 is directed downwards while reading books, for instance, a substantial part of the pupil of the wearer's eye is covered by the central vision correction region 14 functioning as the near vision correction region. Accordingly, the wearer's near vision is effectively corrected owing to the vision correction power of the central vision correction region 14, so that the wearer can obtain clear images of near objects through the central vision correction region 14. When the visual axis of the wearer who wears the contact lens 30 of FIG. 5 is directed frontwards while driving a car, for instance, a substantial part of the pupil is covered by the outer vision correction region 16 functioning as the distant vision correction region, so that the wearer can obtain clear images of distant objects through the outer vision correction region 16.

In the contact lens 30 of this embodiment, it is desirable that the offset distance e of the optical axis P of the vision correction area 12 from the geometric center axis O of the lens (i.e., from the horizontal line L) in the downward direction be 7.0 mm or smaller. This arrangement advantageously assures clear viewing of the near and distant objects in the ordinary daily life of the lens wearer. By taking account of a displacement of the contact lens on the cornea while it is worn on the eye, it is further desirable that the optical axis P of the vision correction area 12 of the contact lens 30 be offset from the geometric center axis O, in the right direction (i.e., to the right of the vertical line M), that is, on the side of the nose of the lens wearer when the contact lens 30 is worn on the eye. Further, the optical power distribution of the vision correction area 12 of the contact lens 30 is preferably determined based on the above formulas (1), (2) and (4)–(11).

Figure 6:
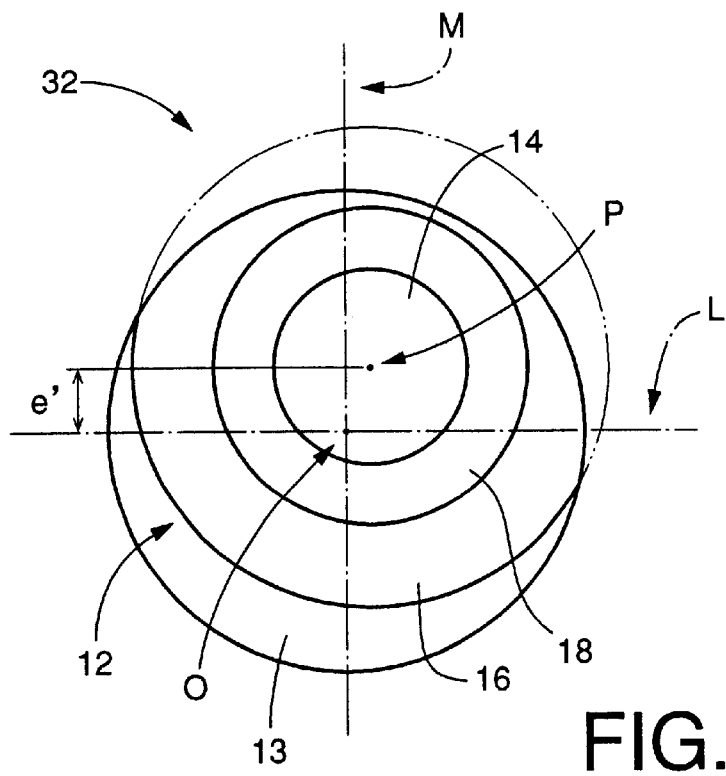
FIG. 6 is a plan view of a contact lens according to a further embodiment of the invention.

Referring next to FIG. 6, there is shown another example of the translating vision type ocular lens in the form of a contact lens 32. In this contact lens 32, the central vision correction region 14 is used as the distant vision correction region while the outer vision correction region 16 is used as the near vision correction region. The optical axis P of the vision correction area 12 including the central, intermediate and outer vision correction regions 14, 16, 18 is offset from the geometric center axis O (i.e., from the horizontal line L) in the upward direction by a distance e', as shown in FIG. 6.

In the thus constructed contact lens 32, too, the distant vision correction region and the near vision correction region are selectively used depending upon the movement of the visual axis of the lens wearer, i.e., the position of of the center of the pupil of the eye, to thereby assure clear viewing of both of the distant and near objects through the vision correction area 12. In this contact lens 32, the offset distance e' of the optical axis P of the vision correction area 12 from the geometric center axis O (i.e., from the horizontal line L) in the upward direction is preferably determined to be 7.0 mm or smaller, so that the wearer who wears the thus constructed contact lens 32 can obtain clear images of the distant and near objects through the vision correction area 12 in the ordinary daily life.

In this contact lens 32, too, by taking account of the displacement of the lens on the cornea while it is worn on the eye, it is desirable that the optical axis P of the vision correction area 12 be also offset from the geometric center axis O, in the right direction (i.e., to the right of the vertical line M), that is, on the side of the nose of the wearer when the lens 32 is worn on the eye. Further, the optical power distribution of the contact lens 32 is preferably determined based on the above formulas (1), (2) and (12) through (19).

Figure 7:
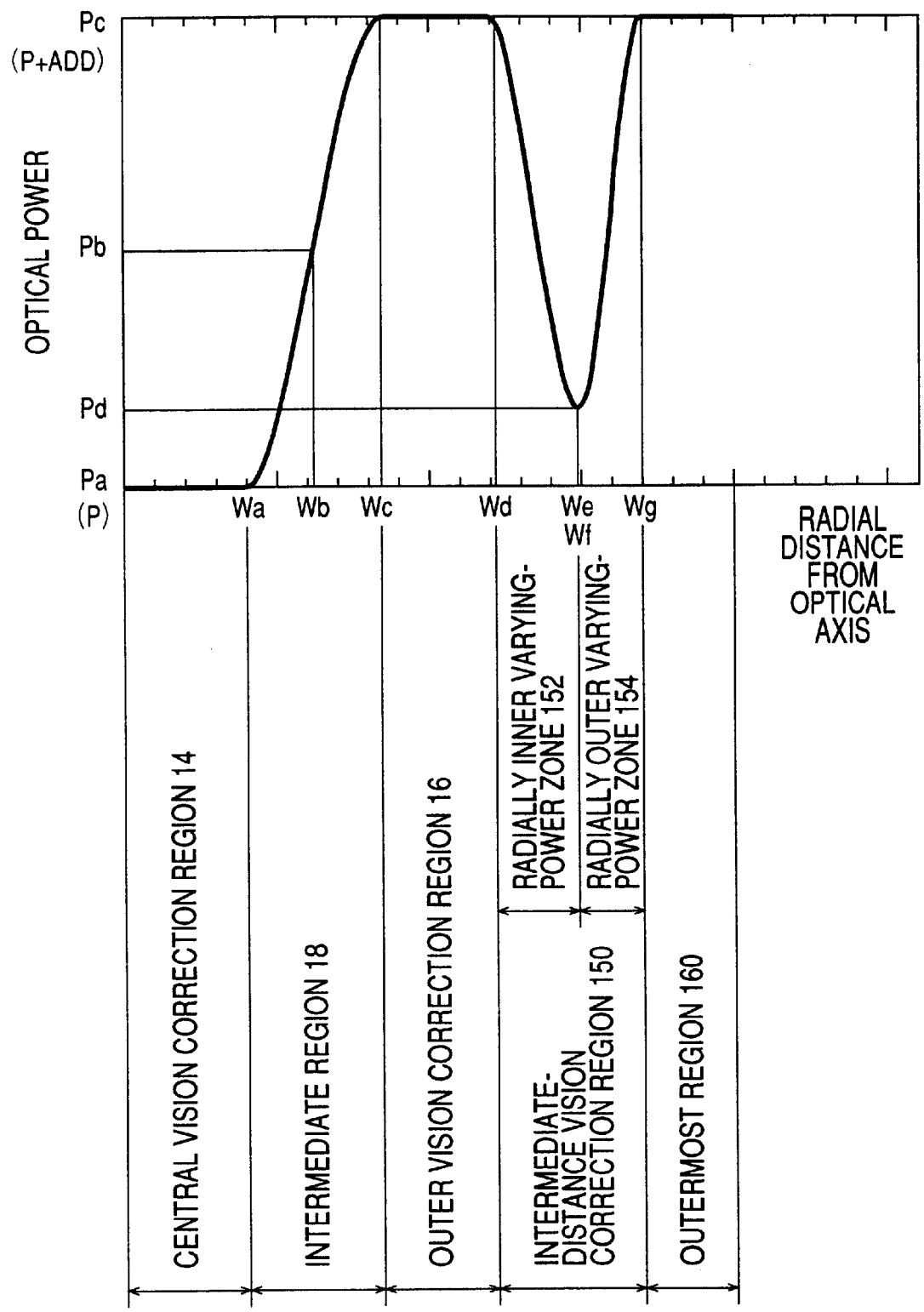
FIG. 7 is a graph showing another example of the optical power distribution of the contact lens of the present invention.

In the above-described contact lenses 10, 30, 32, 40, the vision correction area 12 may further include an intermediate-distance vision correction region 150 for improving the visual acuity at the intermediate distance between the near and distant distances. This intermediate-distance vision correction region 150 is located radially outwardly of and adjacent to the outer vision correction region 16, as shown in FIG. 7 by way of example. The intermediate-distance vision correction region 150 comprises a radially inner and outer varying-power zones 152, 154, and has a distribution of optical power which is intermediate between the optical power values of the central and outer vision correction regions 14, 16. FIGS. 7–12 show various patterns of the optical power distribution of the intermediate-distance vision correction region 150.

Described more specifically, the intermediate-distance vision correction region 150 comprises the radially inner and outer varying-power zones 152, 154. In the radially inner varying-power zone 152, the optical power varies in the radial direction of the lens from the optical power value Pc of the outer vision correction region 16 to a desired predetermined value Pd which is between the optical power values Pa, Pc of the central and outer vision correction regions 14, 16. In the radially outer varying-power zone 154, the optical power varies in the radial direction of the lens from the predetermined value Pd to the optical power value Pc of the outer vision correction region 16. The optical power in at least one of the radially inner and outer varying-power zones 152, 154 is represented by one polynomial of the second or higher order, or a combination of two different polynomials of the second or higher order.

In the present embodiment, a value y3 of the optical power in the radially inner varying-power zone 152 is represented by the following equation (20), while a value y4 of the optical power in the radially outer varying-power zone 154 is represented by the following equation (21), $$y3 = E1 \cdot (x^3/3 - x^2(Wd+We)/2 + x \cdot Wd \cdot We) + F1 \quad (20)$$

$$y4 = E2 \cdot (x^3/3 - x^2(Wf+Wg)/2 + x \cdot Wf \cdot Wg) + F2 \quad (21)$$

wherein, $E1 = (Pc-Pd)/((Wd^3-We^3)/3 - (Wd^2-We^2)(Wd+We)/2 + (Wd-We) \cdot Wd \cdot We)$ $F1 = Pc - E1 \cdot (Wd^3/3 - Wd^2(Wd+We)/2 + Wd \cdot Wd \cdot We)$ $E2 = (Pd-Pc)/((Wf^3-Wg^3)/3 - (Wf^2-Wg^2)(Wf+Wg)/2 + (Wf-Wg) \cdot Wf \cdot Wg)$ $F2 = Pd - E2 \cdot (Wf^3/3 - Wf^2(Wf+Wg)/2 + Wf \cdot Wf \cdot Wg)$ and wherein, x: a radial distance from the optical axis P of the vision correction area 12;

Wd: a radial distance from the optical axis P to a boundary between the outer and intermediate-distance vision correction regions 16, 150;

We: a radial distance from the optical axis P to a radially outer end of the radially inner varying-power zone 152;

Wf: a radial distance from the optical axis P to a radially inner end of the radially outer varying-power zone 154;

Wg: a radial distance from the optical axis P to a radially outer end of the radially outer varying-power zone 154;

Pc: the optical power value of the outer vision correction region 16;

Pd: the predetermined optical power value in the intermediate-distance vision correction region 150.

Figure 8:
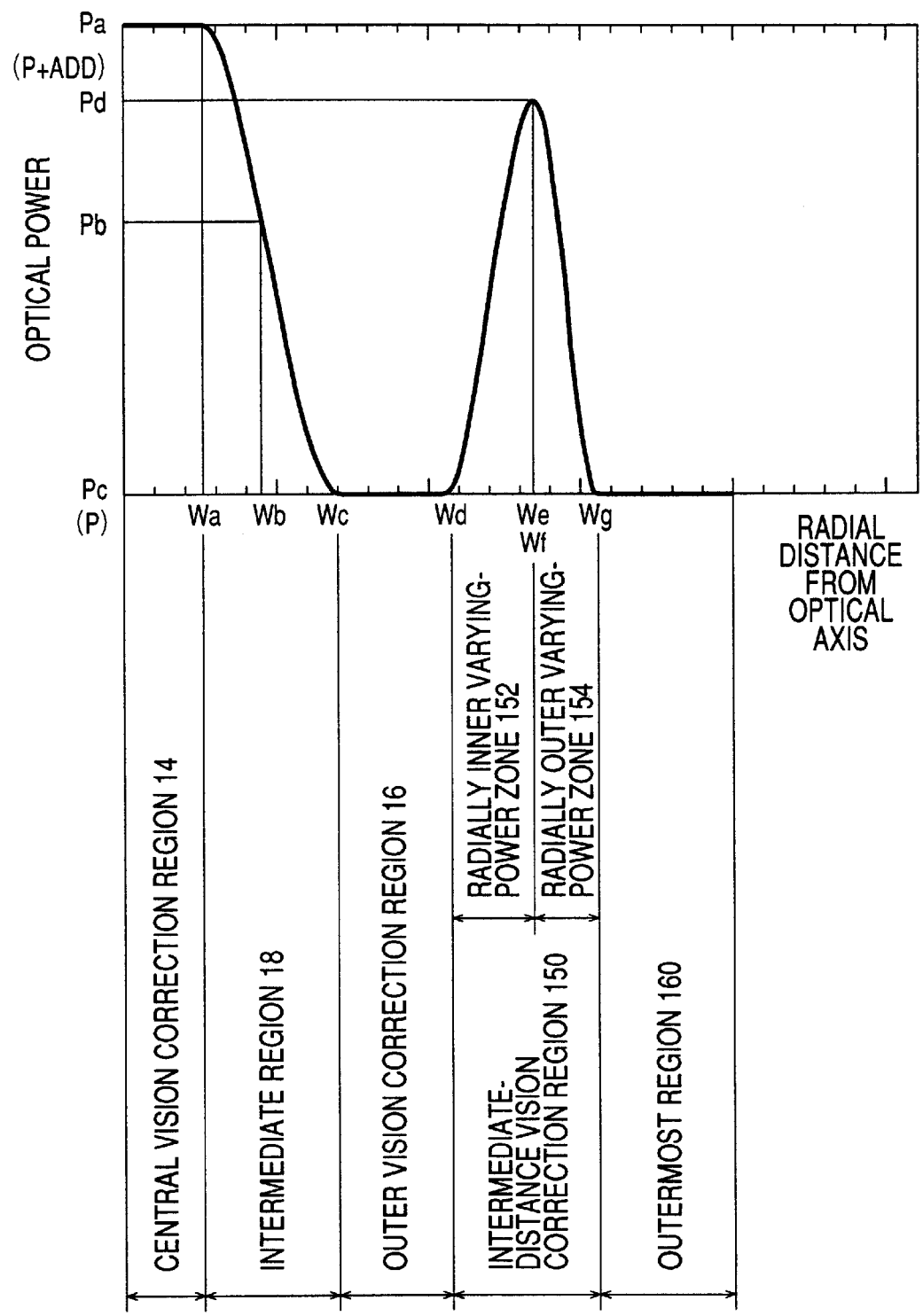
FIG. 8 is a graph showing still another example of the optical power distribution of the contact lens of the present invention.
Figure 9:
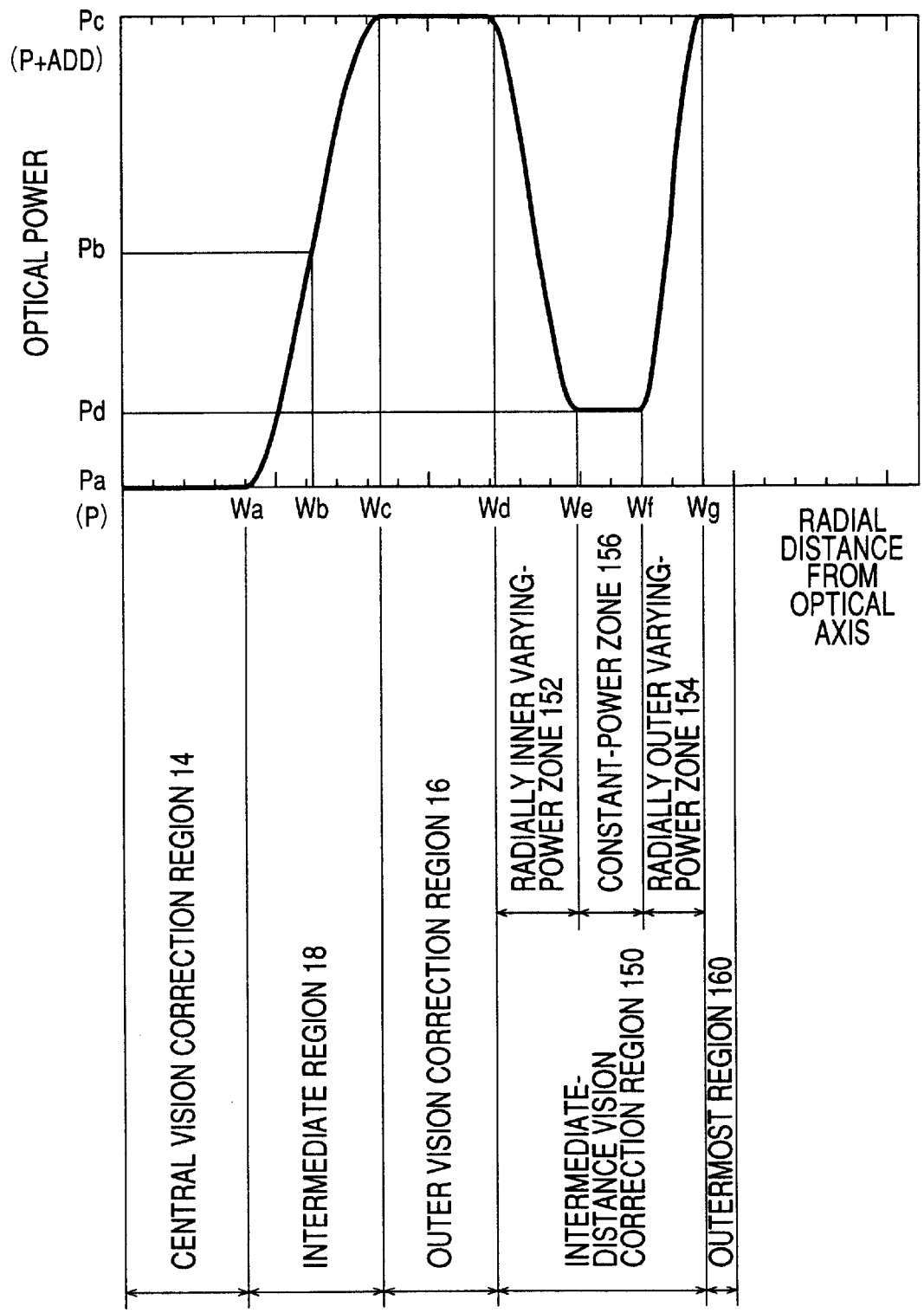
FIG. 9 is a graph showing yet another example of the optical power distribution of the contact lens of the present invention.
Figure 10:
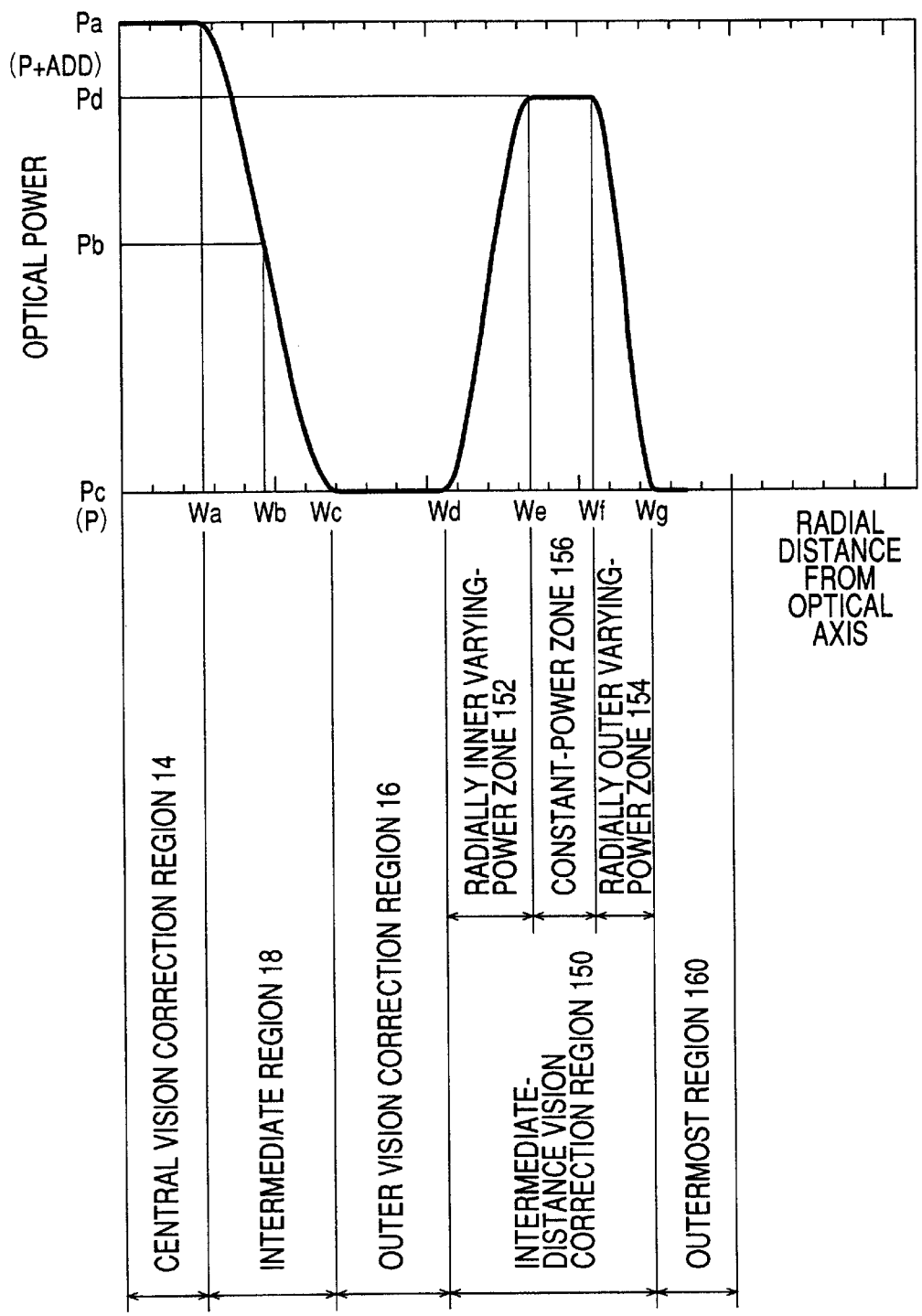
FIG. 10 is a graph showing a further example of the optical power distribution of the contact lens of the present invention.

In the contact lens whose optical power distribution is represented by the graphs of FIGS. 7 and 8, the intermediate-distance vision correction region 150 consists of the radially inner and outer varying-power zones 152, 154 which are connected to and adjacent to each other, such that the optical power at the radially outer end of the radially inner varying-power zone 152 and the optical power at the radially inner end of the radially outer varying-power zone 154 are both equal to the predetermined value Pd. Alternatively, the intermediate-distance vision correction region 150 may consist of the radially inner and outer varying-power zones 152, 154 and a constant-power zone 156 interposed therebetween, as shown in the graphs of FIGS. 9 and 10. This constant-power zone 156 extends over a suitable radial distance between the radially inner and outer varying-power zones 152, 154, and has a constant optical power over its entire area. The constant optical power in the constant-power zone 156 is equal to the optical powers at the radially outer end of the radially inner varying-power zone 152 and the radially inner end of the radially outer varying-power zone 154, i.e., the predetermined optical power value Pd. The optical power in the constant-power zone 156 is represented by one algebraic equation of the zeroth order.

In the present contact lens having the intermediate-distance vision correction region 150, when the central and outer vision correction regions 14, 16 are used as the distant and near vision correction regions, respectively, the radial distance Wd, namely, the distance from the optical center axis P of the vision correction area 12 to the boundary between the outer and intermediate-distance vision correction regions 16, 150, is held in the range of 1.0–4.0 mm, and the radial dimension of the intermediate-distance vision correction region 150 is held in the range of 0.4–3.0 mm. When the central and outer vision correction regions 14, 16 are used as the near and distant vision correction regions, respectively, the radial distance Wd is held in the range of 0.6–3.0 mm, and the radial dimension of the intermediate-distance vision correction region 150 is held in the range of 0.4–3.0 mm.

Figure 11:
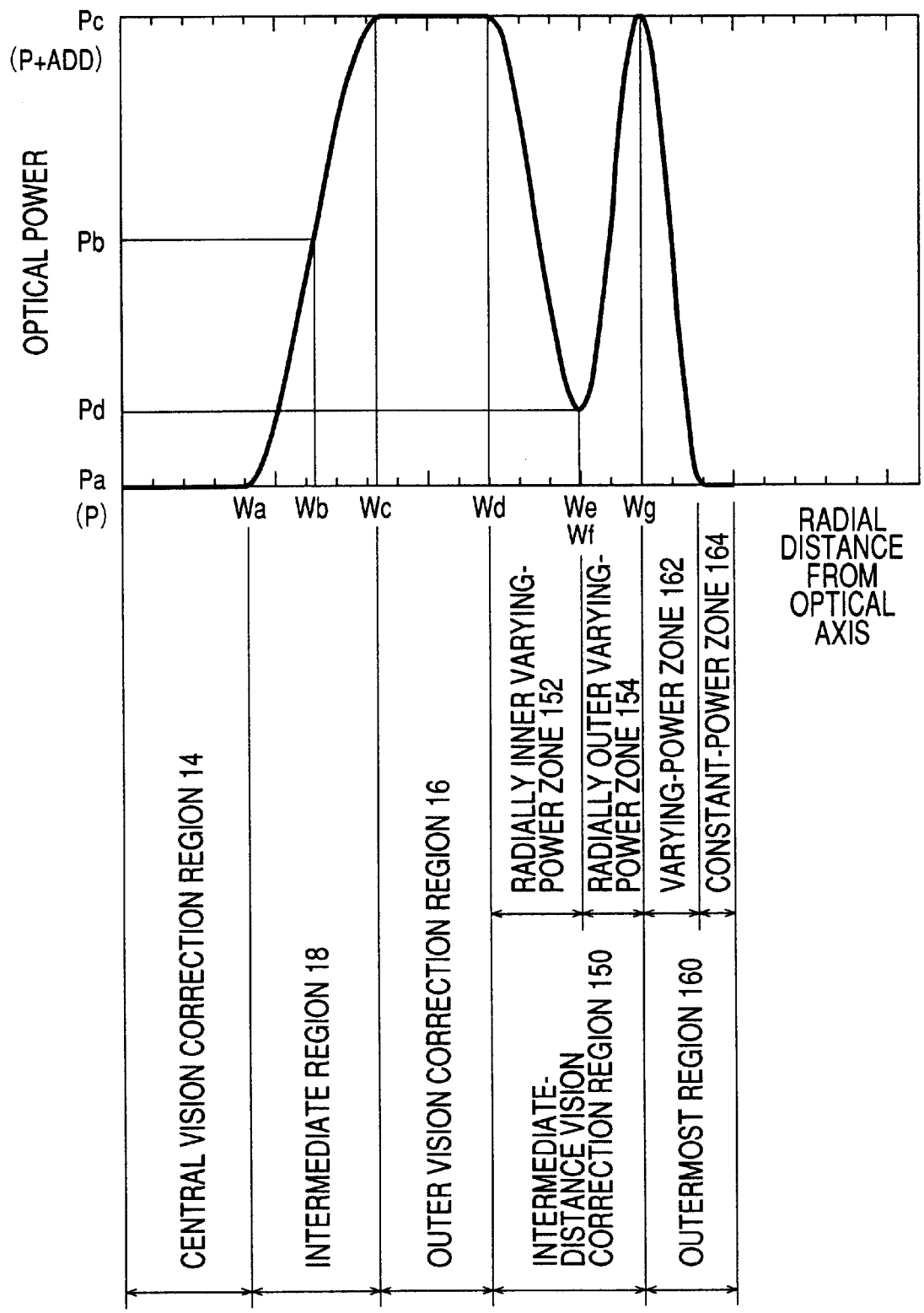
FIG. 11 is a graph showing a still further example of the optical power distribution of the contact lens of the present invention.
Figure 12:
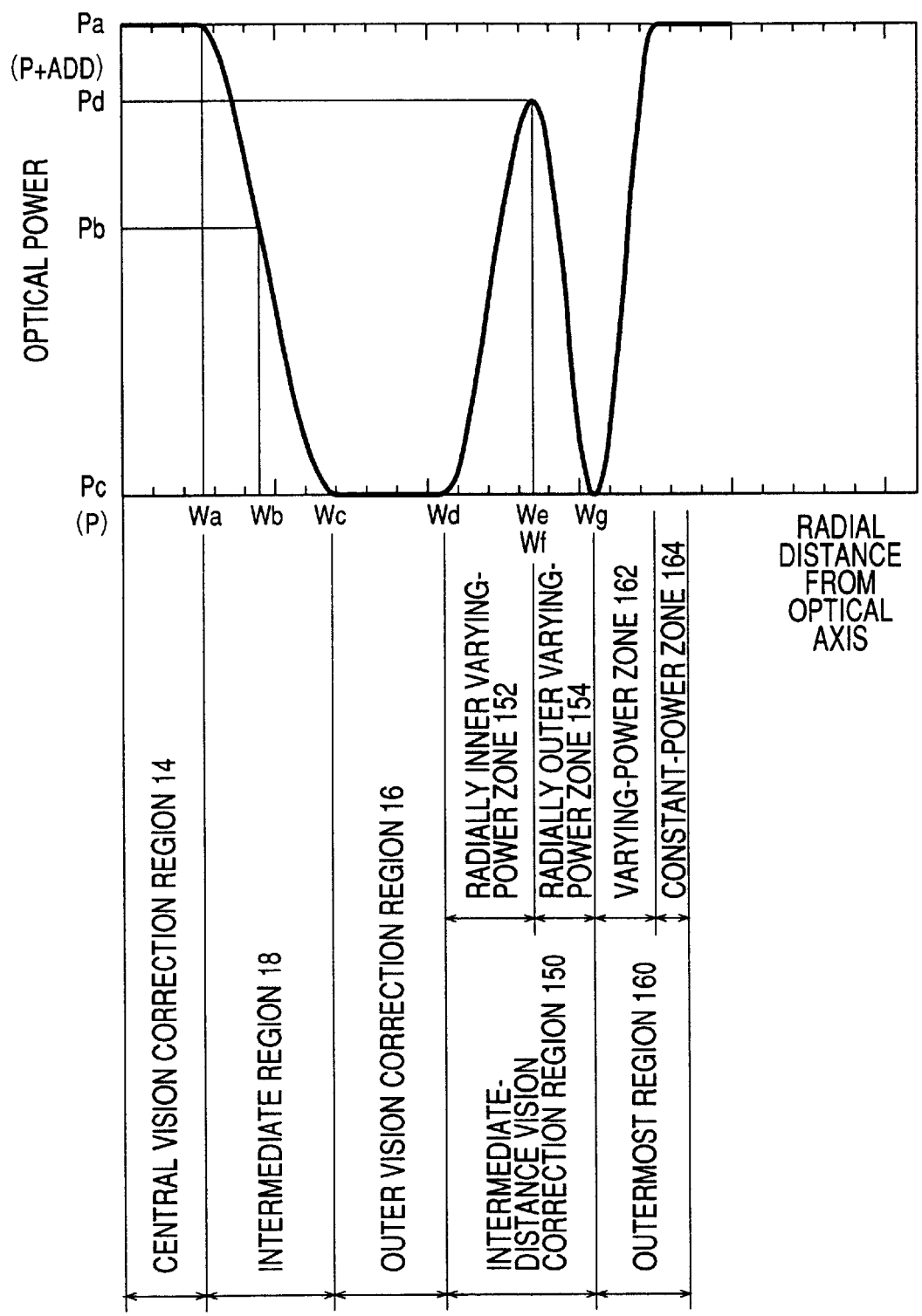
FIG. 12 is a graph showing a yet further example of the optical power distribution of the contact lens of the present invention.

In the contact lens of the present embodiment, the vision correction area 12 may further include an outermost vision correction region 160 which is located radially outwardly of and adjacent to the intermediate-distance vision correction region 150. As shown in the graphs of FIGS. 7–10, this outermost region 160 may be constituted by a single constant-power zone having a constant optical power which is represented by one algebraic equation of the zeroth order. The optical power of the outermost region 160 constituted by the single constant-power zone is equal to the optical power value Pc of the outer vision correction region 16, to thereby enhance the visual acuity of objects at the desired distance to which the optical power value Pc of the outer vision correction region 16 is tuned. Alternatively, as shown in the graphs of FIGS. 11 and 12, the outermost region 160 may be constituted by a varying-power zone 162 and a constant-power zone 164. The varying-power zone 162 has an optical power which is represented by one polynomial of the second or higher order or a combination of two different polynomials of the second or higher order. The varying-power zone 162 formed in the outermost region 160 is effective to reduce or avoid the problem of ghosting or double imaging. The constant-power zone 164 has a constant optical power which is represented by one algebraic equation of the zeroth order. The constant optical power of the constant-power zone 164 is equal to the optical power Pa of the central vision correction region 14, to thereby enhance the visual acuity of objects at the desired distance to which the optical power value Pa of the central vision correction region 14 is tuned.

Figure 13:
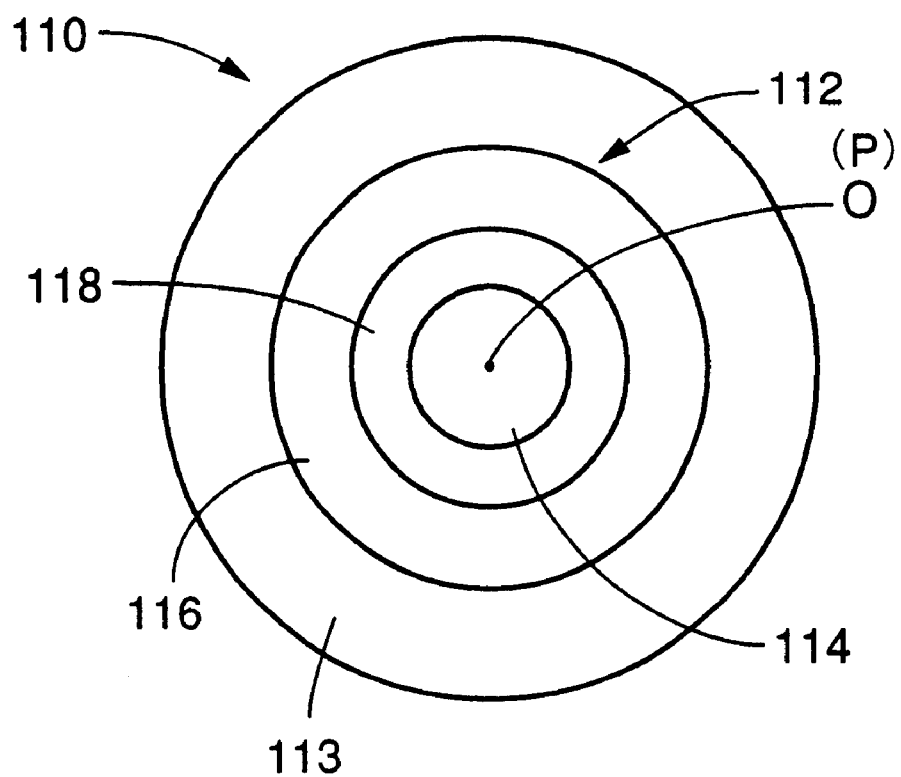
FIG. 13 is a plan view of a contact lens according to another embodiment of the invention.

Referring next to FIG. 13, there is shown a multifocal ocular lens in the form of a contact lens 110 for correction of presbyopia, for instance, which lens is constructed according to a further embodiment of the present invention. This contact lens 110 includes a vision correction area 112 whose optical axis P is aligned with a geometric center axis O of the lens which is a center of a circle defined by the periphery of the lens. A portion 113 radially outward of the vision correction area 112, in other words, the radially outermost portion 113 of the contact lens 110, is not to be located on the pupil of the eye of the user when the contact lens 110 is worn on the eye. Accordingly, this radially outermost portion 113 does not have any optical significance, but is provided for easy and stable fitting of the lens on the eye. The portion 113 of the lens 110 is subjected to a slab-off machining as needed.

The vision correction area 112 includes a circular central vision correction region 114 whose center is aligned with the above-described optical axis P, an annular outer vision correction region 116 located concentrically with and radially outwardly of the central vision correction region 114 with a suitable radial distance therebetween, and an annular intermediate vision correction region 118 located concentrically with and interposed between the central and outer vision correction regions 114, 116. These three regions 114, 116, 118 have respectively determined mutually different values of optical power.

The central and outer vision correction regions 114, 116 have respective constant values of optical power which are different from each other. Depending upon the user's visual requirements and lifestyle or living environment, for example, the central and outer vision correction regions 114, 116 are used, respectively, as one and the other of a near vision correction region for correcting the user's near vision, through which near objects are observed, and a distant vision correction region for correcting the user's distant vision, through which distant objects are observed. The intermediate vision correction region 118 has a varying optical power, which gradually varies in the radial direction of the lens, such that the optical power smoothly changes between the mutually different optical power values of the central and outer vision correction regions 114, 116. That is, the optical power of the lens 110 smoothly continuously changes from that of the central vision correction region 114 to that of the outer vision correction region 116 via the continuously varying optical power value of the intermediate region 118.

The optical powers of the central and outer vision correction regions 114, 116 are represented by respective different algebraic equations or expressions of the zeroth degree or order in relation to the radial distance from the optical axis P. In other words, the optical powers of the central and outer vision correction regions 114, 116 are constant, irrespective of a change of the radial distance from the optical axis P. The optical power of the intermediate region 118 is represented by one polynomial equation whose degree is not smaller than 2, and continuously changes from the optical power value of the central vision correction region 114 to that of the outer vision correction region 116 with an increase of the radial distance from the optical axis P. Thus, the lens power distribution in the vision correction area 112 which consists of the central, intermediate and outer vision correction regions 114, 116, 118 is determined.

Described more specifically, the optical power y of the intermediate region 118 at its radial point which is distant from the optical axis P of the vision correction area 112 by a radial distance x is represented by the following polynomial equation (26):

$$y=(Pa-Pb)\times(x-Wb)^{exp}/(Wa-Wb)^{exp}+Pb \qquad (26)$$

wherein,

Pa: the optical power of the central vision correction region 114,

Pb: the optical power of the outer vision correction region 114,

Wa: a radial distance from the optical axis P of the vision correction area 112 to a boundary of the central vision correction region 114 and the intermediate region 118, Wb: a radial distance from the optical axis P of the vision correction area 112 to a boundary of the intermediate region 118 and the outer vision correction region 116, and exp: the degree of the polynomial equation, which represents a rate of change of the optical power of the intermediate region 118.

The surface of the contact lens is determined according to the above arrangement such that the intermediate region 118 is smoothly continuously connected to the outer vision correction region 116, so that the optical power smoothly continuously changes from the varying value of the intermediate region 118 to the value Pb of the outer vision correction area 116 near the boundary of the two regions. Accordingly, the present contact lens is free from the problem of the ghosting or double imaging, and assures the user of a comfortable wearing.

Figure 14:
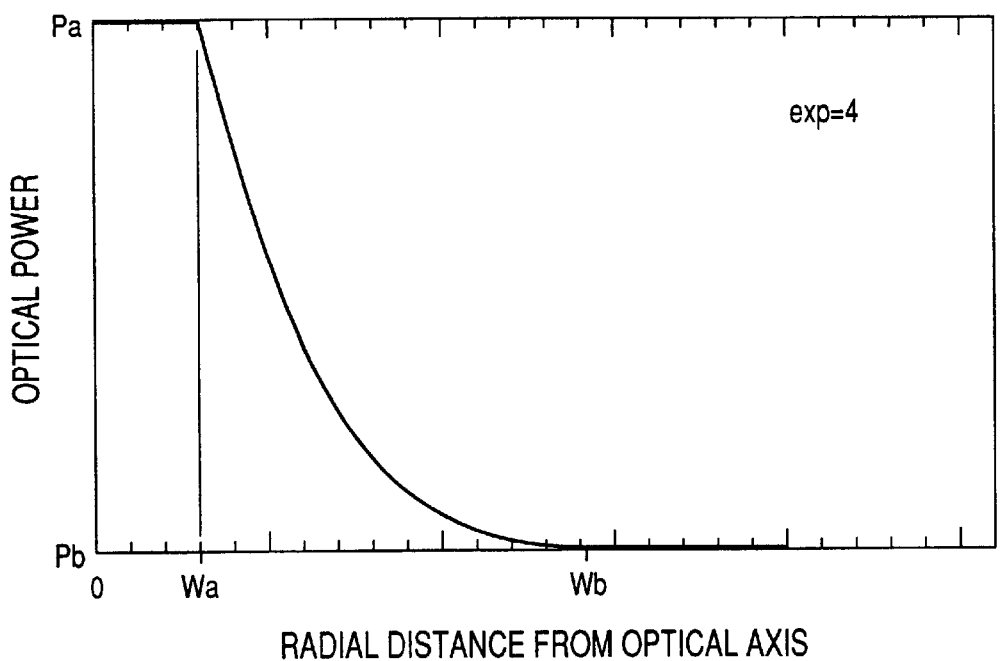
FIG. 14 is a graph showing one example of a distribution of the optical power of the contact lens of FIG. 13, in the radial direction, wherein the optical power of an intermediate region of the lens smoothly changes to that of an outer vision correction region of the lens.
Figure 15:
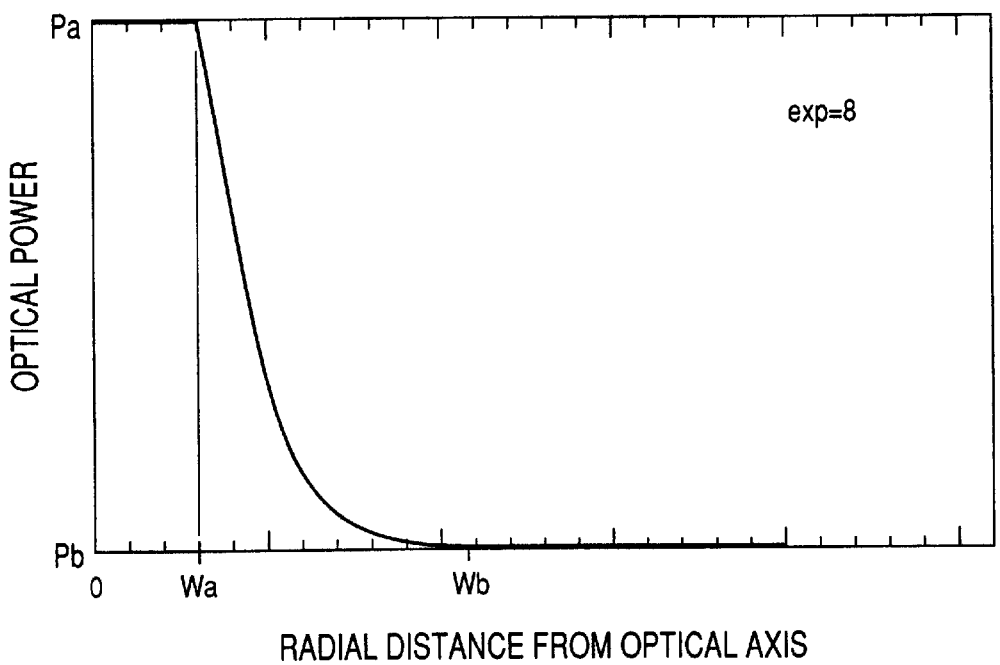
FIG. 15 is a graph showing another example of the distribution of the optical power of the contact lens of FIG. 13, in the radial direction, wherein the optical power of the intermediate region smoothly changes to that of the outer vision correction region.
Figure 16:
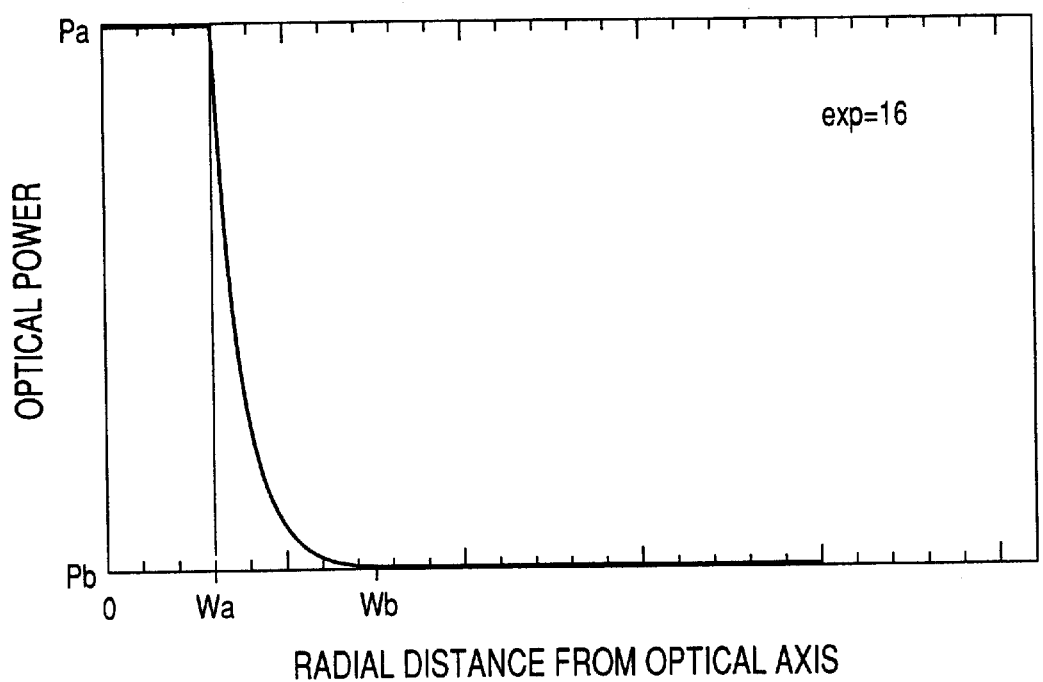
FIG. 16 is a graph showing still another example of the distribution of the optical power of the contact lens of FIG. 13, in the radial direction, wherein the optical power of the intermediate region smoothly changes to that of the outer vision correction region.

Various lens power distributions determined according to the above formula (26) are shown in graphs of FIGS. 14–16. The degree (order) exp of the polynomial equation, which represents the rate of change of the optical power of the intermediate region 118 is 4, 8, and 16 in the graphs of FIGS. 14, 15, and 16, respectively. As is apparent from these graphs, the rate of change of the optical power of the intermediate region 118, and the optical characteristics of the contact lens can be effectively adjusted as desired, by changing the degree exp of the polynomial equation (26).

The lens power distribution may be otherwise determined. For instance, the optical power y of the intermediate region 118 at its radial point which is distant from the optical axis P of the vision correction area 112 by a radial distance x is represented by the following polynomial equation (29) by using coefficients E and F represented by formulas (27) and (28) below, respectively:

$$E=(Pa-Pb)/((Wa^{exp}-Wb^{exp})/\exp-(Wa^{exp-1}-Wb^{exp-1})\times(Wa+Wb)/(\exp-1)+(Wa^{exp-2}-Wb^{exp-2})\times Wa\times Wb/(\exp-2)) \quad (27)$$

$$F=Pa-E\times(Wa^{exp}/\exp-Wa^{exp-1}\times(Wa+Wb)/(\exp-1)+Wa^{exp-2}\times Wa\times Wb/(\exp-2)) \quad (28)$$

$$y=E\times(X^{exp}/\exp-X^{exp-1}\times(Wa+Wb)/(\exp-1)+x^{exp-2}\times Wa\times Wb/(\exp-2))+F \quad (29)$$

wherein, Pa, Pb, Wa, Wb, and exp are the same as described above with respect to the above polynomial equation (26).

The surface of the contact lens is determined according to the above arrangement such that the intermediate region 118 is smoothly continuously connected to both of the central and outer vision correction regions 114, 116, so that the optical power continuously changes from the value Pa of the central vision correction region 114 to the value Pb of the outer vision correction region 116 via the continuously varying optical power of the intermediate region 118. Accordingly, the present contact lens is free from the problem of the ghosting or double imaging, and assures the user of a comfortable wearing.

Figure 17:
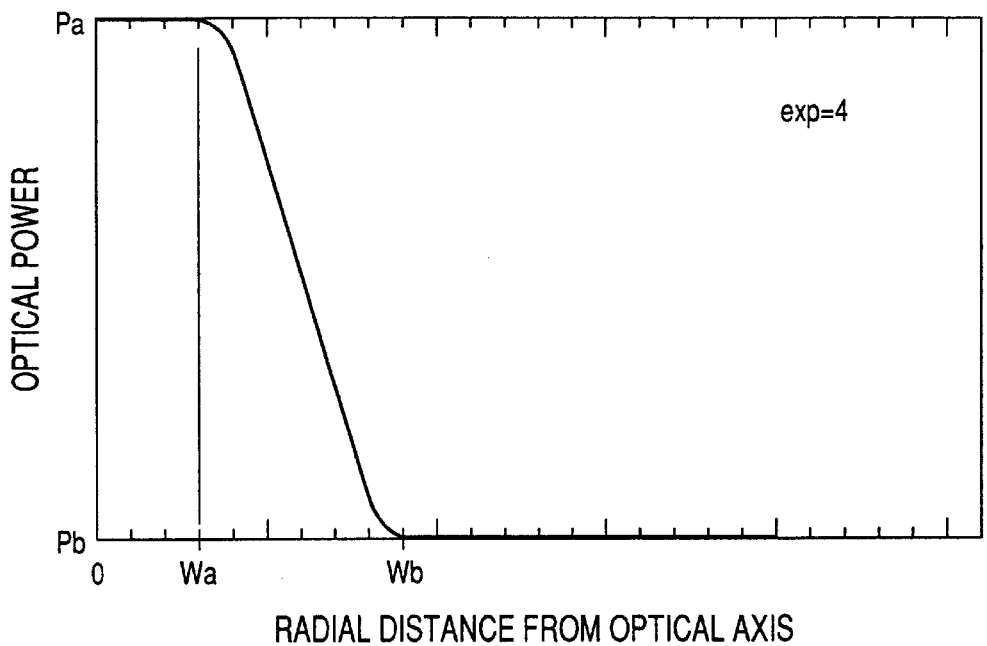
FIG. 17 is a graph showing one example of the distribution of the optical power of the contact lens of FIG. 13, in the radial direction, wherein the optical power of the intermediate region smoothly changes to those of the central and outer vision correction regions.
Figure 18:
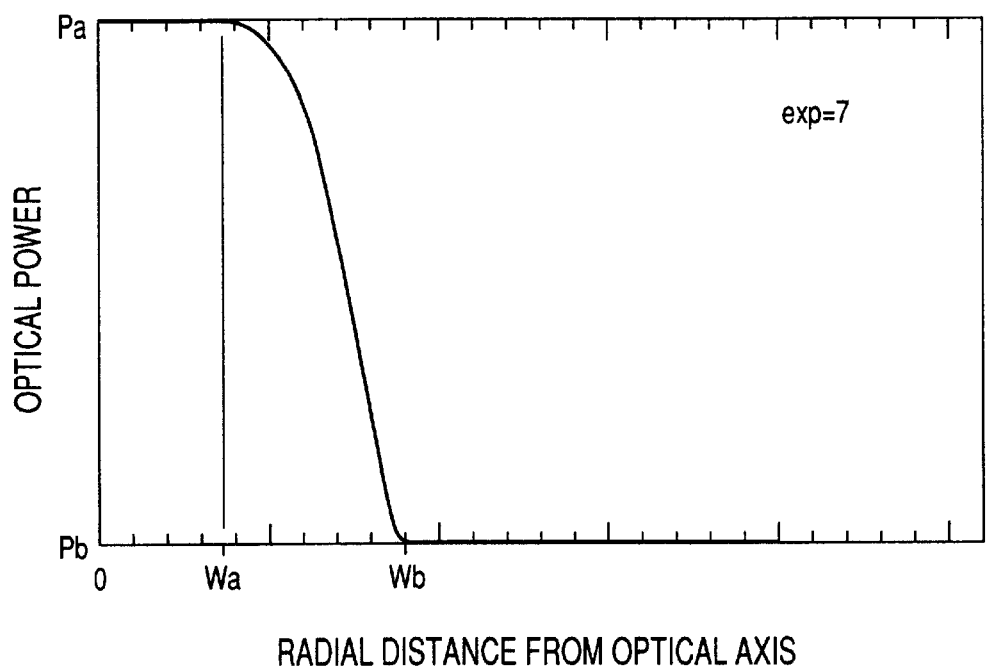
FIG. 18 is a graph showing another example of the distribution of the optical power of the contact lens of FIG. 13, in the radial direction, wherein the optical power of the intermediate region smoothly changes to those of the central and outer correction visions; region therebetween.
Figure 19:
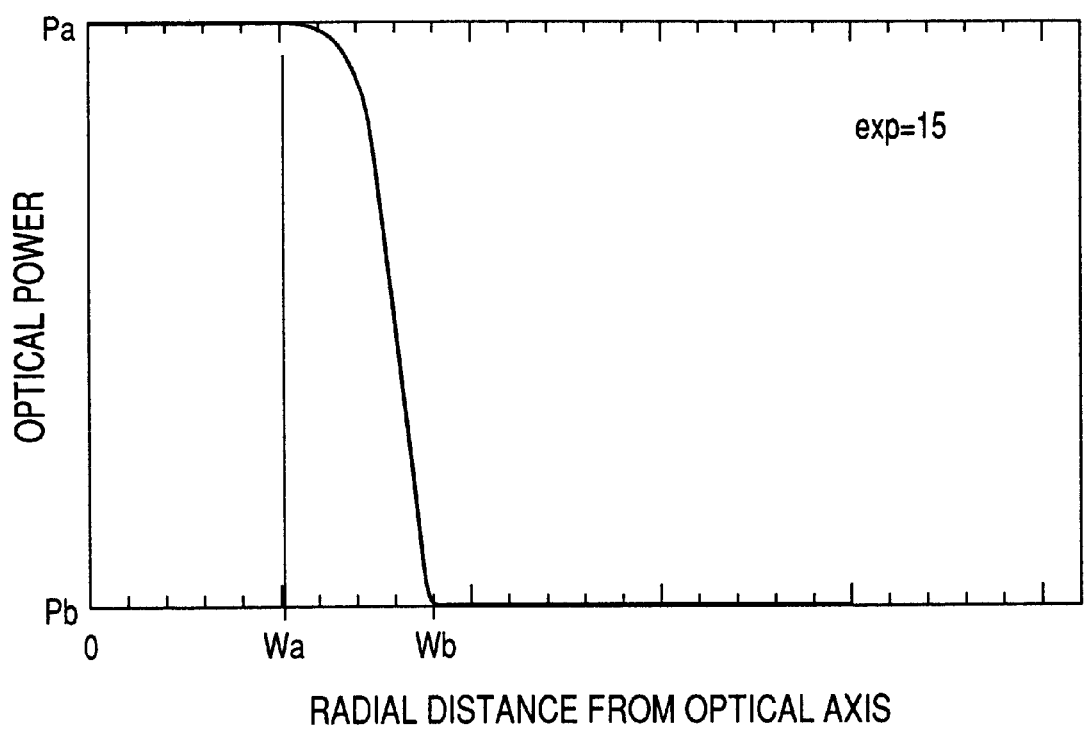
FIG. 19 is a graph showing another example of the distribution of the optical power of the contact lens of FIG. 13, in the radial direction, wherein the optical power of the intermediate region smoothly changes to those of the central and outer correction visions.

The various lens power distributions determined according to the above polynomial equation (29) are shown in graphs of FIGS. 11–13. The degree exp of the polynomial equation, which represents the rate of change of the optical power of the intermediate region 118 is 4, 7, and 15 in the graphs of FIGS. 17, 18, and 19, respectively. As is apparent from these graphs, the rate of change of the optical power of the intermediate region 118, and the optical characteristics of the contact lens can be effectively adjusted as desired, by changing the degree exp of the polynomial equation (29).

The lens power distributions may be further otherwise determined. For instance, the optical power y of the intermediate region 118 at its radial point which is distant from the optical axis P of the vision correction area 112 by a radial distance x is represented by the following polynomial equation (30):

$$y=(Pb-Pa)\times(x-Wa)^{exp}/(Wb-Wa)^{exp}+Pa \quad (30)$$

wherein, Pa, Pb, Wa, Wb, and exp are the same as described above with respect to the above polynomial equation (26).

The surface of the contact lens is determined according to the above arrangement such that the intermediate region 118 is smoothly continuously connected to the central vision correction region 114, so that the optical power smoothly continuously changes from the value of the central vision correction region 114 to that of the intermediate vision correction region 118 near the boundary of the two regions 114, 118. Accordingly, the present contact lens is free from the problem of the ghosting or double imaging, and assures the user of a comfortable wearing.

Figure 20:
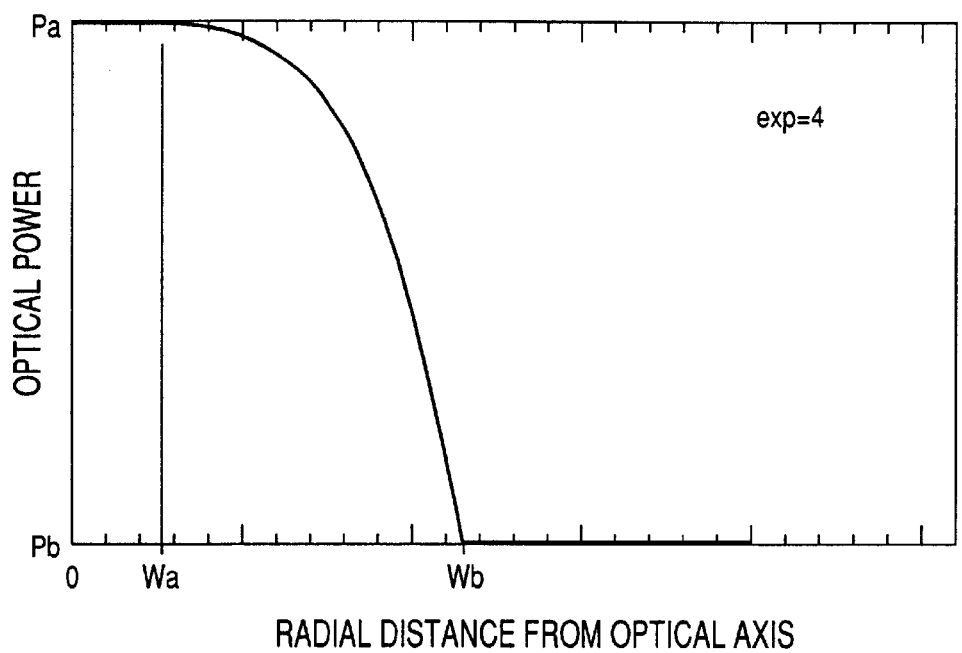
FIG. 20 is a graph showing one example of the distribution of the optical power of the contact lens of FIG. 13, in the radial direction, wherein the optical power of the intermediate region smoothly changes to that of the central vision correction region.
Figure 21:
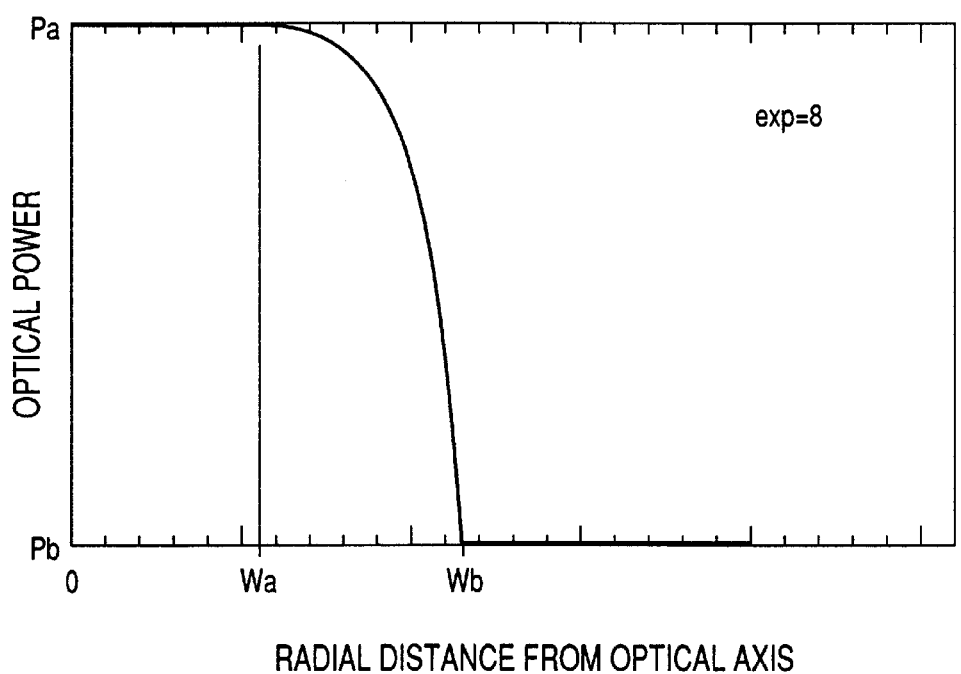
FIG. 21 is a graph showing another example of the distribution of the optical power of the contact lens of FIG. 13, in the radial distance, wherein the optical power of the intermediate region smoothly changes to that of the central vision correction region.
Figure 22:
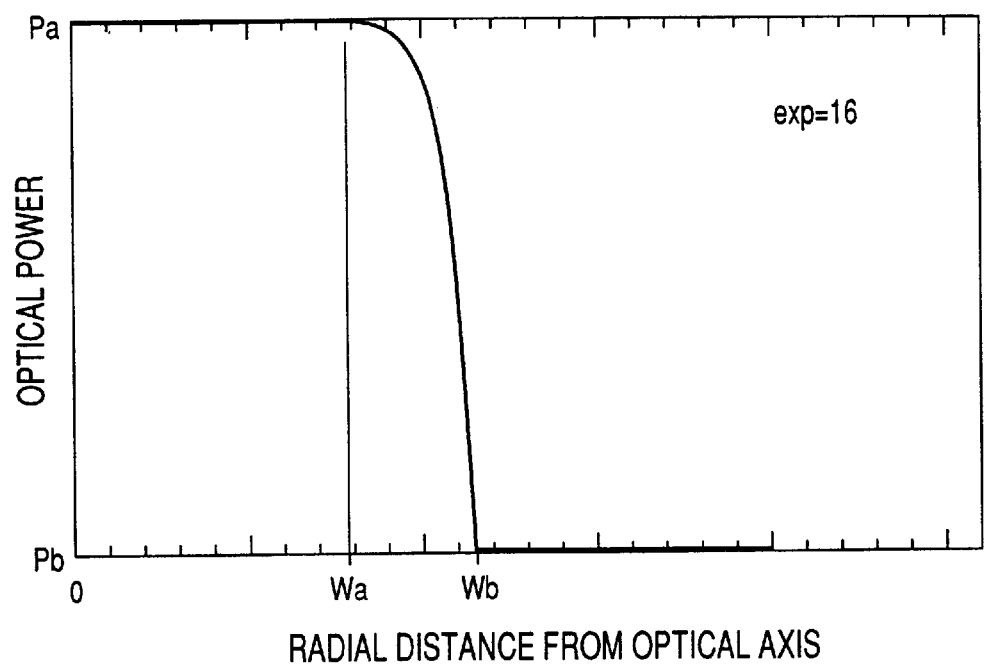
FIG. 22 is a graph showing still another example of the distribution of the optical power of the contact lens of FIG. 13, in the radial distance, wherein the optical power of the intermediate region smoothly changes to that of the central vision correction region.

The various lens power distributions determined according to the above equation (30) are shown in graphs of FIGS. 20–22. The degree exp of the polynomial equation, which represents the rate of change of the optical power of the intermediate region 118 is 4, 8, and 16 in the graphs of FIGS. 20, 21, and 22, respectively. As is apparent from these graphs, the rate of change of the optical power of the intermediate region 118, and the optical characteristics of the contact lens can be effectively adjusted as desired, by changing the degree exp of the polynomial equation (30).

As is apparent from the above-indicated various examples of the lens power distributions of the present multifocal contact lens 110 determined according to the formulas (26)–(30) and shown in the graphs of FIGS. 14–22, the central vision correction region 114 having the constant optical power Pa constitutes a substantial part of a central optical zone of the lens 110 used for near vision correction, while the outer vision correction region 116 having the constant optical power Pb constitutes a substantial part of a peripheral optical zone used for distant vision correction. Accordingly, the thus designed contact lens 110 is capable of assuring a high degree of clearness of images of both of the near and distant objects observed through the central and peripheral optical zones, respectively. The radial dimensions of the vision correction regions 114, 116, 118 of the lens 110 are suitably determined so as to meet the user's visual requirements, and assure the user of a comfortable wearing or fitting of the lens, while satisfying the above formulas (22) through (24).

In the contact lenses 110 having the various optical power distributions shown in the graphs of FIGS. 14–22, the central vision correction region 114 serves as the near vision correction region, while the outer vision correction region 116 serves as the distant vision correction region. According to the present invention, the central vision correction region 114 may be used as the distant vision correction region, and the outer vision correction region 116 may be used as the near vision correction region, depending upon the user's visual requirements. In this case, too, the optical power of the intermediate region 118 is preferably determined based on the formula (26), the formulas (27)–(29) or the formula (30).

The configuration of the contact lens 110 whose optical power is designed as described above is determined such that the inner surface of the lens 110 to be in contact with the cornea of the user's eye has a part-spherical profile following that of the cornea, and such that the outer surface is shaped according to a ray tracing method, so as to give an intended optical power distribution.

In the contact lens 110 shown in FIG. 13, the optical axis P of the vision correction area 112 is aligned with the geometrical center axis O of the contact lens 110. However, the optical axis P may be offset from the geometrical center axis O, as needed. In this case, depending upon the offset distance of the optical axis P from the geometrical center axis O, and the radial dimensions of the respective vision correction regions 114, 116, 118, the circular vision correction area 112 may be partly removed at its radially outer peripheral portion, generally, at the radially outer peripheral portion of the outer vision correction region 116, but possibly at the radially outer peripheral portion of the intermediate vision correction region 116, and even at the radially outer peripheral portion of the central vision correction region 114.

Figure 23:
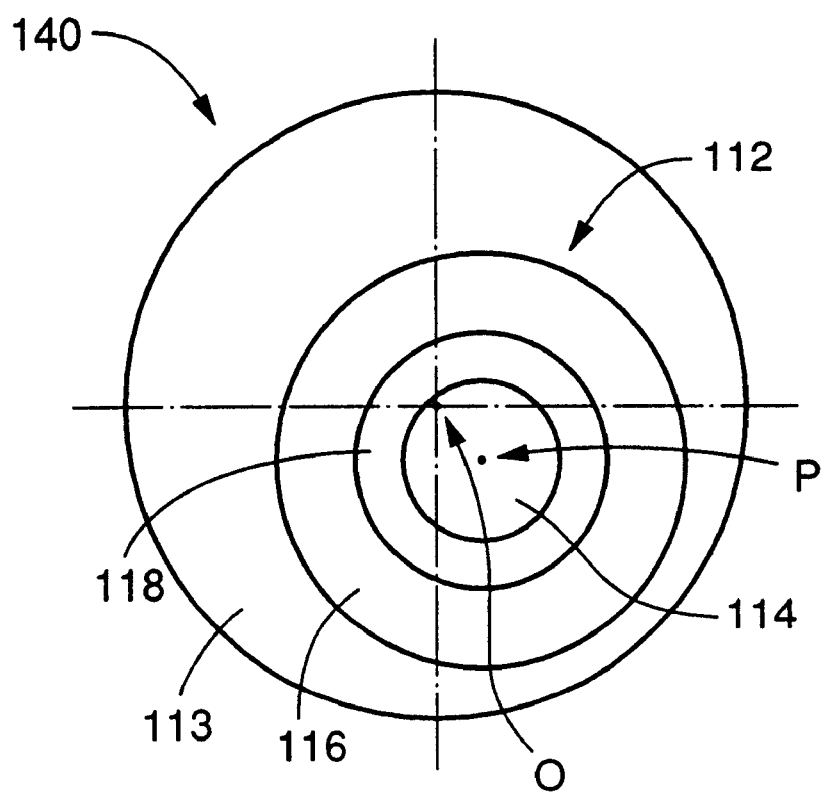
FIG. 23 is a plan view of a contact lens according to another embodiment of the invention.

For instance, the optical axis P of the vision correction area 112 of a contact lens 140 is offset from the geometrical center axis O as shown in FIG. 23, such that the optical axis P is shifted in the right direction as seen in FIG. 23, on the side of the nose of the wearer when the contact lens is worn on the eye, and is also shifted in the downward direction. The optical axis P is shifted from the geometrical center axis O of the lens on the side of the nose of the lens wearer, in view of a fact that the contact lens tends to be moved toward a portion of the cornea on the side of the ear of the wearer when the lens is worn on the eye, since the cornea of the human eye has a larger curvature at the portion on the side of the ear than the other portion on the side of the nose. Further, the optical axis P is shifted from the geometrical center axis O of the lens in the downward direction, in view of a tendency that the visual axis of the lens wearer usually is directed downwards in the ordinary daily life. When the contact lens whose optical axis P is offset from its geometric center axis O as described above is worn on the eye of the user, the optical axis P is easily aligned with the center of the pupil, so that the contact lens effectively achieves the intended vision correction function. For easy understanding, the same reference numerals as used in the contact lens of FIG. 23 are used to identify the corresponding portions of the contact lens 140 of FIG. 23.

Though the contact lenses 110, 140 of the above-described embodiments are the simultaneous vision type, the multifocal ocular lens of the present invention is also used as the translating vision type ocular lens, by suitably determining the offset distance of the optical axis of the vision correction regions 114, 116, 118 (vision correction area 112) from the geometric center axis of the lens, and the size or the radial dimensions of the respective vision correction regions.

Figure 24:
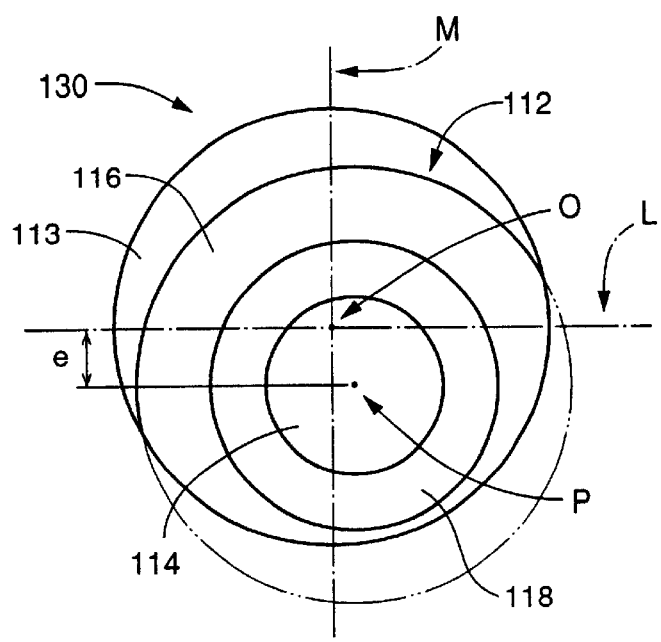
FIG. 24 is a plan view of a contact lens according to still another embodiment of the invention.

Referring to FIG. 24 there is shown still another embodiment of the multifocal ocular lens according to the present invention, in the form of a translating vision type contact lens 130. In the contact lens 130 of this embodiment, the central vision correction region 114 is used as the near vision correction region while the outer vision correction region 116 is used as the distant vision correction region. The vision correction area 112 which consists of the central, intermediate and outer vision correction regions 114, 116, 118 has an optical axis P which is offset from the geometric center axis O of the lens in the downward direction as seen in FIG. 24, wherein a line indicated by "L" is a horizontal line passing the geometric center axis O of the lens, and a line indicated by "M" is a vertical line also passing the geometric center axis O.

When the visual axis of the wearer who wears the thus constructed contact lens 130 is directed downwards while reading books, for instance, a substantial part of the pupil of the wearer's eye is covered by the central vision correction region 114 functioning as the near vision correction region. Accordingly, the wearer's near vision is effectively corrected owing to the vision correction power of the central vision correction region 114, so that the wearer can obtain clear images of near objects through the central vision correction region 114. When the visual axis of the wearer who wears the contact lens 130 of FIG. 24 is directed frontwards while driving a car, for instance, a substantial part of the pupil is covered by the outer vision correction region 116 functioning as the distant vision correction region, so that the wearer can obtain clear images of distant objects through the outer vision correction region 116.

In the contact lens 130 of this embodiment, it is desirable that the offset distance e of the optical axis P of the vision correction area 112 from the geometric center axis O of the lens (i.e., from the horizontal line L) in the downward direction be 7.0 mm or smaller. This arrangement advantageously assures clear viewing of the near and distant objects in the ordinary daily life of the lens wearer. By taking account of a displacement of the contact lens on the cornea while it is worn on the eye, it is further desirable that the optical axis P of the vision correction area 112 of the contact lens 130 be offset from the geometric center axis O, in the right direction (i.e., to the right of the vertical line M in FIG. 18), that is, on the side of the nose of the lens wearer when the contact lens 130 is worn on the eye.

Figure 25:
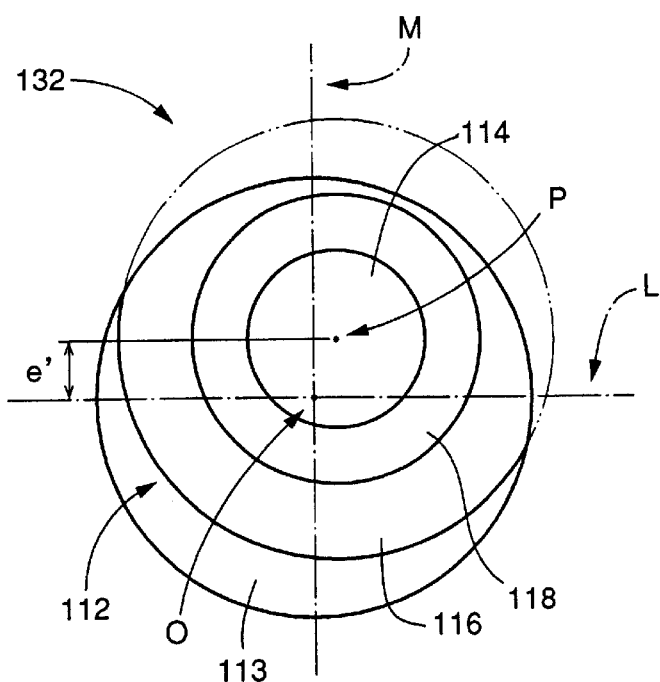
FIG. 25 is a plan view of a contact lens according to a further embodiment of the invention.

Referring next to FIG. 25, there is shown another example of the translating vision type ocular lens in the form of a contact lens 132. In this contact lens 132, the central vision correction region 114 is used as the distant vision correction region while the outer vision correction region 116 is used as the near vision correction region. The optical axis P of the vision correction area 112 including the central, intermediate and outer vision correction regions 114, 116, 118 is offset from the geometric center axis O (i.e., from the horizontal line L) in the upward direction by a distance e', as shown in FIG. 25.

In the thus constructed contact lens 132, too, the distant vision correction region and the near vision correction region are selectively used depending upon the movement of the visual axis of the lens wearer, i.e., the position of of the center of the pupil of the eye, to thereby assure clear viewing of both of the distant and near objects. In this contact lens 132, the offset distance e' of the optical axis P of the vision correction area 112 from the geometric center axis O (i.e., from the horizontal line L) in the upward direction is preferably determined to be 7.0 mm or smaller, so that the wearer who wears the thus constructed contact lens 132 can obtain clear images of the distant and near objects (through the vision correction area 112) in the ordinary daily life.

In this contact lens 132, too, by taking account of the displacement of the lens on the cornea while it is worn on the eye, it is desirable that the optical axis P of the vision correction area 112 be also offset from the geometric center axis O, in the right direction as seen in FIG. 25, that is, on the side of the nose of the wearer when the lens 132 is worn on the eye.

While the present invention has been described in detail its presently preferred embodiments, it is to be understood that the invention may be otherwise embodied.

Each of the contact lenses of the illustrated embodiments is preferably provided with suitable rotation preventive means for preventing rotational displacement of the lenses in its circumferential direction during use in contact with the cornea, especially when the contact lens has the optical axis P which is offset from the geometrical center axis O of the lens. As such rotation preventive means, a so-called "prism ballast" mechanism is preferably employed. The contact lens which employs the prism ballast mechanism has a gravity center at a relatively lower portion thereof, by increasing the thickness of the lower portion, whereby the contact lens is prevented from moving in the circumferential direction on the cornea while it is worn thereon, so that the lens is retained in position on the cornea by gravity with high stability.

In the illustrated embodiments, the vision correction regions have a circular or an annular shape whose center is aligned with the optical axis P. However, these regions may be otherwise shaped, such as an ellipsoidal shape.

When either one of the lens surfaces has a toric portion, the optical power of the lens may vary in its circumferential direction. In this case, the rate of change of the optical power in the intermediate region may vary in the corresponding circumferential direction of the lens.

The material of the contact lenses of the illustrated embodiments is not particularly limited. For instance, the contact lens of the present invention may be formed of rigid gas-impermeable polymethyl methacrylate (PMMA), materials known for forming hard lenses, such as a rigid gas-permeable silicone/acrylate copolymer, and materials known for forming soft lenses.

The contact lens of the present invention may be produced according to any known methods. For instance, the contact lens may be produced by a cutting operation, wherein an intended lens is cut from a lens blank to have desired inner and outer surfaces. The contact lens may be molded by using a suitable mold assembly having molding surfaces which respectively give the desired inner and outer surfaces of the intended lens. Further, one of the inner and outer surfaces of the lens is formed by molding, while the other surface is formed by cutting. In another method, a precursor of the intended lens is first obtained by molding, and then the precursor of the lens is subjected to a cutting operation to provide the desired inner and outer surfaces of the intended lens. The cutting operation permits stable production of the contact lens having a highly accurate surface configuration, while the molding assures improved production efficiency of the contact lens. If the cutting operation and the molding are effected in combination to produce the contact lens, the contact lens with an accurate surface configuration can be obtained with high production efficiency.

The principle of the present invention is applicable to various kinds of contact lenses and intraocular lenses, other than the presbyopia correction contact lenses.

It is to be understood that the present invention is not limited to the details of the illustrated embodiments, but may be embodied with various changes, modifications and improvements, which may occur to those skilled in the art, without departing from the scope of the invention define in the following claims.

What is claimed is:

1. A multifocal ocular lens having a vision correction area consisting of a plurality of vision correction regions having respective different values of optical power, said plurality of vision correction regions including a central vision correction region, an outer vision correction region, and an intermediate region located between said central and outer vision correction regions, said vision correction area having an optical axis with which centers of said central and outer vision correction regions are aligned, said intermediate region consisting of a radially inner transition section adjacent to said central vision correction region and a radially outer transition section adjacent to said outer vision correction region, said central and outer vision correction regions having respectively determined first and second mutually different optical power values (Pa, Pc), said optical power of said intermediate region changing from said first value to said second value, such that a rate of change of said optical power of said radially inner transition section increases with an increase in a radial distance from said optical axis of said vision correction area of said lens, along a first quadratic curve, while a rate of change of said optical power of said radially outer transition section increases with an increase in a radial distance from a radially inner periphery of said outer vision correction region, along a second quadratic curve, said first and second quadratic curves being connected to each other at a point of inflection which corresponds to a radial position of a boundary between said radially inner and outer transition sections, and which corresponds to a desired third optical power value (Pb) between said first and second values, and wherein said optical axis of said vision correction area of said lens is offset from a geometric center axis of said lens in a lateral direction by a distance of not larger than 2.0 mm, and also in a vertical direction by a distance of not larger than 7.0 mm.

2. A multifocal ocular lens according to claim 1, wherein a value y1 of said optical power of said radially inner transition section at a radial point which is distant from said optical axis of said vision correction area of said lens by a radial distance x1 is represented by the following equation (1), while a value y2 of said optical power of said radially outer transition section at a radial point which is distant from said optical axis of said vision correction area by a radial distance x2 is represented by the following equation (2), $$y1=Pa-(Pa-Pb)\times(Wa-x1)^2/(Wa-Wb)^2 \qquad (1)$$

$$y2=Pc-(Pc-Pb)\times(Wc-x2)^2/(Wc-Wb)^2 \qquad (2)$$

wherein,

Pa: said first value of said optical power of said central vision correction region, Pc: said second value of said optical power of said outer vision correction region, Pb: said third value of said optical power at said radial position of said boundary between said radially inner and outer transition sections, Wa: a radial distance from said optical axis of said vision correction area to a boundary between said central vision correction region and said radially inner transition section, Wb: a radial distance from said optical axis of said vision correction area to said boundary between said radially inner and outer transition sections, and Wc: a radial distance from said optical axis of said vision correction area to a boundary of said radially outer transition section and said outer vision correction region.

3. A multifocal ocular lens according to claim 2, wherein said radial distance Wb from said optical axis of said vision correction area to said boundary of said radially inner and outer transition sections is determined according to the following equation:

$$Wb=((Pa-Pb)Wc-(Pc-Pb)Wa)/(Pa-Pc) \qquad (3).$$

4. A multifocal ocular lens according to claim 2, wherein said central vision correction region constitutes a part of a central optical zone for correction of a near vision, while said outer vision correction region constitutes a part of a peripheral optical zone for correction of a distant vision, and values Pa, Pb, Pc, Wa, Wb and Wc in said equations (1) and (2) are determined as follows:

$$Pa=P+ADD \qquad (4)$$

$$P+(\tfrac{1}{6})ADD \leq Pb \leq P+(\tfrac{2}{3})ADD \qquad (5)$$

$$Pc=P \qquad (6)$$

$$Wa=(\tfrac{1}{2})SD \qquad (7)$$

$$(\tfrac{1}{2})SD+(\tfrac{1}{8})IM \leq Wb \leq (\tfrac{1}{2})SD+(\tfrac{1}{2})IM \qquad (8)$$

$$Wc=(\tfrac{1}{2})SD+IM \qquad (9)$$

$$0.1 \text{ mm} \leq IM \leq 3.5 \text{ mm} \qquad (10)$$

$$0 \leq SD \leq 8.0 \text{ mm} \qquad (11)$$

wherein,

ADD: a difference between Pa and Pc,

IM: a radial dimension of said intermediate region,

SD: a diameter of said central optical zone, and

OZ: a diameter of said peripheral optical zone.

5. A multifocal ocular lens according to claim 2, wherein said central vision correction region constitutes a part of a central optical zone for correction of a distant vision, while said outer vision correction region constitutes a part of a peripheral optical zone for correction of a near vision, and values Pa, Pb, Pc, Wa, Wb and Wc in said equations (1) and (2) are determined as follows:

$$Pa=P \tag{12}$$

$$P+(\tfrac{1}{6})ADD \leq Pb \leq P+(\tfrac{2}{3})ADD \tag{13}$$

$$Pc=P+ADD \tag{14}$$

$$Wa=(\tfrac{1}{2})SD \tag{15}$$

$$(\tfrac{1}{2})SD+(\tfrac{1}{2})IM \leq Wb \leq (\tfrac{1}{2})SD+(\tfrac{7}{8})IM \tag{16}$$

$$Wc=(\tfrac{1}{2})SD+IM \tag{17}$$

$$0.1 \text{ mm} \leq IM \leq 3.5 \text{ mm} \tag{18}$$

$$0 \leq SD \leq 8.0 \text{ mm} \tag{19}$$

wherein,
ADD: a difference between Pa and Pc,
IM: a radial dimension of said intermediate region,
SD: a diameter of said central optical zone, and
OZ: a diameter of said peripheral optical zone.

6. A multifocal ocular lens according to claim 1, wherein at least one of opposite surf aces of said lens has part-spherical portions corresponding to said central and outer vision correction regions.

7. A multifocal ocular lens having a vision correction area consisting of a plurality of vision correction regions having respective different values of optical power, said plurality of vision correction regions including a central vision correction region, an outer vision correction region, and an intermediate region located between said central and outer vision correction regions, said vision correction area having an optical axis with which centers of said central and outer vision correction regions are aligned, said intermediate region consisting of a radially inner transition section adjacent to said central vision correction region and a radially outer transition section adjacent to said outer vision correction region, said central and outer vision correction regions having respectively determined first and second mutually different optical power values (Pa, Pc), said optical power of said intermediate region changing from said first value to said second value, such that a rate of change of said optical power of said radially inner transition section increases with an increase in a radial distance from said optical axis of said vision correction area of said lens, along a first quadratic curve, while a rate of change of said optical power of said radially outer transition section increases with an increase in a radial distance from a radially inner periphery of said outer vision correction region, along a second quadratic curve, said first and second quadratic curves being connected to each other at a point of inflection which corresponds to a radial position of a boundary between said radially inner and outer transition sections, and which corresponds to a desired third optical power value (Pb) between said first and second values, said vision correction area further including an intermediate-distance vision correction region located radially outwardly of and adjacent to said outer vision correction region and having a distribution of optical power between said first and second values (Pa, Pc) of said central and outer vision correction regions, respectively, and wherein said intermediate-distance vision correction region comprises a radially inner varying-power zone and a radially outer varying-power zone, and the optical power in said radially inner varying-power zone continuously varying in a radial direction of said lens from said second optical power value (Pc) of said outer vision correction region to a predetermined fourth optical power value (Pd) which is between said first and second optical power values (Pa, Pc) of said central and outer vision correction regions, while the optical power in said radially outer varying-power zone continuously varies in said radial direction from said fourth optical power value (Pd) to said second optical power value (Pc) of said outer vision correction region.

8. A multifocal ocular lens according to claim 7, wherein a value y3 of the optical power in said radially inner varying-power zone is represented by the following equation (20):

$$y3=E1 \cdot (x^3/3-x^2(Wd+We)/2+x \cdot Wd \cdot We)+F1 \tag{20}$$

wherein, $$E1=(Pc-Pd)/((Wd^3-We^3)/3-(Wd^2-We^2)(Wd+We)/2+(Wd-We) \cdot Wd \cdot We)$$

$$F1=Pc-E1 \cdot (Wd^3/3-Wd^2(Wd+We)/2+Wd \cdot Wd \cdot We)$$

and wherein,
x: a radial distance from said optical axis of said vision correction area;
Wd: a radial distance from said optical axis to a boundary between said outer and intermediate-distance vision correction regions;
We: a radial distance from said optical axis to a radially outer end of said radially inner varying-power zone;
Pc: said second optical power value of said outer vision correction region;
Pd: said fourth optical power value in said intermediate-distance vision correction region.

9. A multifocal ocular lens according to claim 7, wherein a value y4 of the optical power in said radially outer varying-power zone is represented by the following equation (21):

$$y4=E2 \cdot (x^3/3-x^2(Wf+Wg)/2+x \cdot Wf \cdot Wg)+F2 \tag{21}$$

wherein, $$E2=(Pd-Pc)/((Wf^3-Wg^3)/3-(Wf^2-Wg^2)(Wf+Wg)/2+(Wf-Wg) \cdot Wf \cdot Wg)$$

$$F2=Pd-E2 \cdot (Wf^3/3-Wf^2(Wf+Wg)/2+Wf \cdot Wf \cdot Wg)$$

and wherein,
x: a radial distance from said optical axis of said vision correction area;
Wf: a radial distance from said optical axis to a radially inner end of said radially outer varying-power zone;
Wg: a radial distance from said optical axis to a radially outer end of said radially outer varying-power zone;
Pc: said second optical power value of said outer vision correction region;
Pd: said fourth optical power value in said intermediate-distance vision correction region.

10. A multifocal ocular lens according to claim 7, wherein said intermediate-distance vision correction region consists of said radially inner and outer varying-power zones which are connected to and adjacent to each other, such that the optical power at said radially outer end of said radially inner varying-power zone and the optical power at said radially inner end of said radially outer varying-power zone are both equal to said fourth optical power value (Pd).

11. A multifocal ocular lens according to claim 7, wherein said intermediate-distance vision correction region consists of said radially inner and outer varying-power zones, and a constant-power zone interposed between said radially inner and outer varying-power zones and having a constant optical power which is equal to the optical powers at said radially outer end of said radially inner varying-power zone and said radially inner end of said radially outer varying-power zone and which is equal to said fourth optical power value (Pd), said constant optical power in said constant-power zone being represented by one algebraic equation of the zeroth order.

12. A multifocal ocular lens according to claim 7, wherein at least one of the optical powers in said radially inner and outer varying-power zones is represented by one polynomial of the second or higher order or a combination of two different polynomials of the second or higher order.

13. A multifocal ocular lens according to claim 7, wherein said central vision correction region is used as a distant vision correction region while said outer vision correction region is used as a near vision correction region, and said radial distance Wd is in the range of 1.0–4.0 mm and said intermediate-distance vision correction region has a radial dimension of 0.4–3.0 mm.

14. A multifocal ocular lens according to claim 7, wherein said central vision correction region is used as a near vision correction region while said outer vision correction region is used as a distant vision correction region, and said radial distance Wd is in the range of 0.6–3.0 mm and said intermediate-distance vision correction region has a radial dimension of 0.4–3.0 mm.

15. A multifocal ocular lens according to claim 7, wherein said vision correction area further includes an outermost vision correction region located radially outwardly of and adjacent to said intermediate-distance vision correction region and consisting of a constant-power zone having an optical power which is represented by one algebraic equation of the zeroth order and which is equal to said second optical power value (Pc) of said outer vision correction region.

16. A multifocal ocular lens according to claim 7, wherein said vision correction area further includes an outermost vision correction region located radially outwardly of and adjacent to said intermediate-distance vision correction region and consisting of a varying-power zone and a constant-power zone, said varying-power zone having an optical power which is represented by one polynomial equation of the second or higher order or a combination of two different polynomial equations of the second or higher order, so that the optical power in said varying-power zone continuously varies from said second optical power value (Pc) of said outer vision correction region to said first optical power value (Pa) of said central vision correction region, and said constant-power zone having an optical power which is represented by one algebraic equation of the zeroth order and which is equal to said first optical power value (Pa) of said central vision correction region.

17. A multifocal ocular lens according to claim 7, wherein at least one of opposite surfaces of said lens has part-spherical portions corresponding to said central and outer vision correction regions.

* * * * *